United States Patent [19]

Haun et al.

[11] Patent Number: 5,736,367
[45] Date of Patent: Apr. 7, 1998

[54] VECTORS AND PROKARYOTES WHICH AUTOCATALYTICALLY DELETE ANTIBIOTIC RESISTANCE

[75] Inventors: Shirley L. Haun, Gaithersburg, Md.; Charles K. Stover, Mercer Island, Wash.; Graham Hatfull, Pittsburgh, Pa.; Mark S. Hanson, Columbia, Md.; William R. Jacobs, City Island, N.Y.

[73] Assignee: MedImmune, Inc., Gaithersburg, Md.

[21] Appl. No.: 425,380

[22] Filed: Apr. 20, 1995

Related U.S. Application Data

[63] Continuation-in-part of Ser. No. 861,002, Mar. 31, 1992.
[51] Int. Cl.$^6$ .......................... C12N 15/00; C12N 1/20; C12N 15/09; C12N 15/63
[52] U.S. Cl. .......................... 435/172.3; 435/252.3; 435/320.1; 935/65
[58] Field of Search .................. 435/320.1, 172.3, 435/252.3; 935/65

[56] References Cited

U.S. PATENT DOCUMENTS 5,478,745  12/1995  Samulski et al. .......................... 435/320.1
5,512,452   4/1996  Mekalanos et al. ....................... 435/25

OTHER PUBLICATIONS

Haun et al., "In vivo deletion of antibiotic resistance markers from *Mycobacterium smegmatis* and *M. bovis* BCG using γδ resolvase", 94th General Meeting of the American Society for Microbiology, May 23–27, 1994; Biol. Abstr./RRM 46(8): MT–133.

Stover et al., "New use of BCG for recombinant vaccines", Nature 351:456–460, Jun. 1991.

Camilli et al., "Use of genetic recombination as a reporter of gene expression", Proc. Nat. Acad. Sci. USA 91: 2634–2638, Mar. 1994.

Dale et al., "Gene transfer with subsequent removla of the selection gene from the host genome", Proc. Nat. Acad. Sci. USA 88: 10558–10562, Dec. 1991.

*Primary Examiner*—Mindy Fleisher
*Assistant Examiner*—Bonnie D. Weiss
*Attorney, Agent, or Firm*—Charles J. Herron; Elliot M. Olstein

[57] ABSTRACT

A vector and a prokaryote transformed therewith which includes nucleic acid sequences which make possible the autocatalytic deletion of nucleotide sequences encoding an antibiotic resistance phenotype. The prokaryote can be a bacterium, and in particular a mycobacterium. Such transformed mycobacteria may be employed in vaccines, thereby eliminating the attendant risk of vaccines including antibiotic resistance markers.

14 Claims, 39 Drawing Sheets

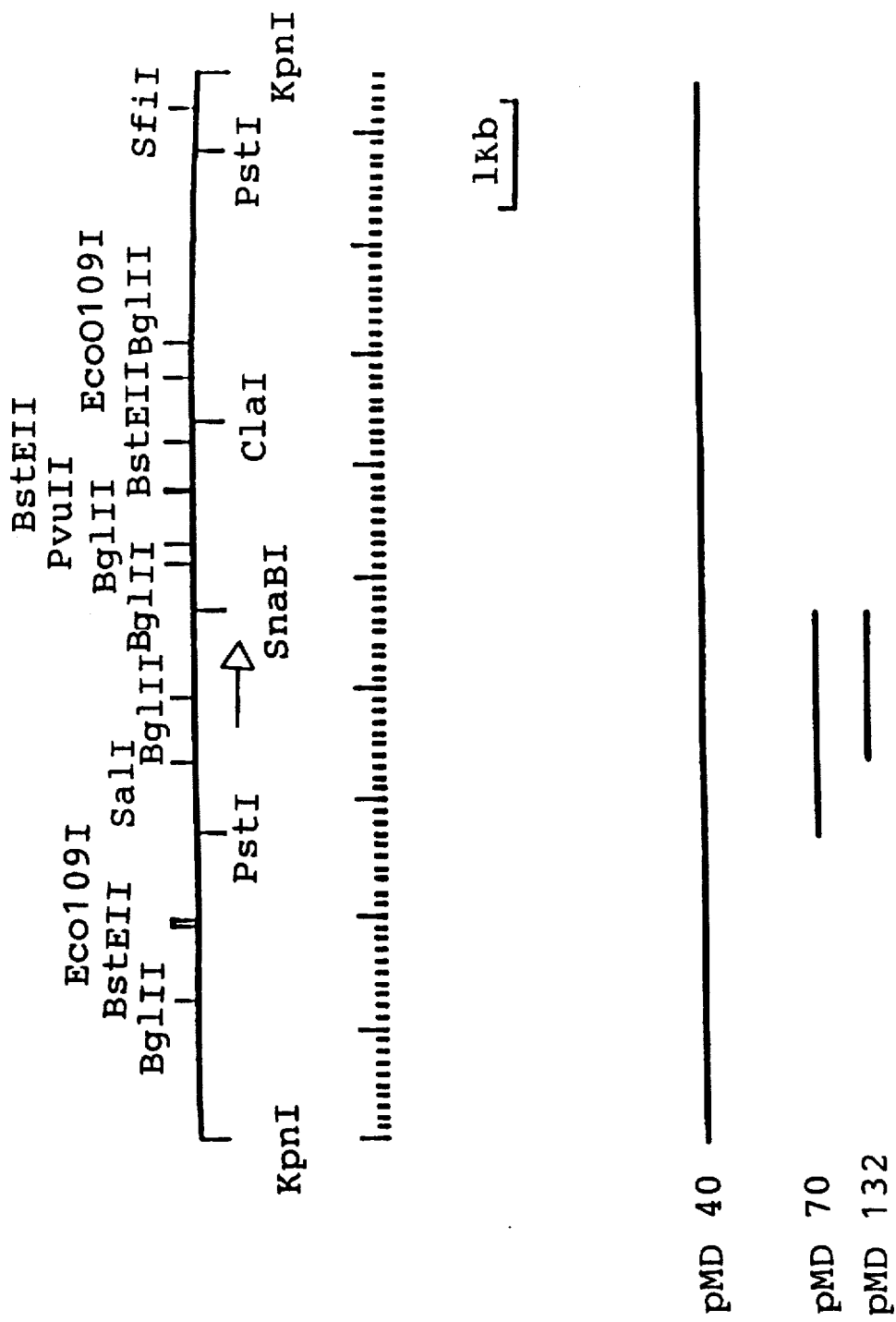

FIG. 6A

```
GTCGACATCGACCTCGAGGAGTACATCAAGAGCTACGGGGTTCGTCGGGCCGCTGTCGGCG        60
AAGTCCGACCTGAAGGAGACCGCCGCCAGTTGGTCGAGTTCGAGTTCGAGGGCCGGA           120
TTCAAGGCGAAGGTACATCTTCGAAACGCCGGTGTGTAACGATCTTGAGGCTGTCTAAGAAAG     180
GAGAGTCGTGACGATGAAACCCGAGTCAACGTGTAACAGAAGGCGACCTAAGTGATACC        240
TGTCACAAGGTTTGCTACCGAGTGGGGCAGGCCGTACATTTACGCCGTAACGCCAG           300
TCGATCCCACGCCCAGTGGGAGACGGCCACGGCCGTCGGGGAACACACCAACTGAATATGGTTC   360
CGCAGACGCAACTAAATTCGGGGTATCCTTGACAGGCCACCAACATGTCTCCGTAATCGGC      420
                             M  S  G  K  I  Q  H  K  A  V

GGAGACGGCACGACCTTTCTCATGGAGGGAAAACATGAGCGGCAAAATCCAACACAAGCAG      480
  V  P  A  P  S  R  I  P  L  T  L  S  E  I  E  D  L  R  R  K
TGGTTCCGGCCCCTAGCCGAATACCACTCTCAGCGAGATCGAAGATCTTCGCAGGA           540
  G  F  N  Q  T  E  I  A  E  L  Y  G  V  T  R  Q  A  V  S  W
AGGGGTTTAATCAGACCGAAATCGCAGAGCTGTATGGCGTGACTCGACAAGCGGTGTCGT        600
  H  K  K  T  Y  G  G  R  L  T  R  Q  I  V  Q  N  W  P
GGCACAAGAAGACCTACGGAGGACGGTTGACCACCAGGCAGATCGTCCAGAACTGGC         660
  W  D  T  R  K  P  H  D  K  S  K  A  F  Q  R  L  R  D  H  G
```

MATCH WITH FIG. 6B

FIG. 6B

MATCH WITH FIG. 6A

```
CGTGGGACACGCGGGAAACCCTCACGATAAGTCGAAGGCTTTTCAGAGGCTCCGGGATCACG    720
  E  Y  M  R  V  G  S  F  R  T  M  S  E  D  K  K  R  L  L
GCGAGTACATGCGAGTGGGTAGCTTCCGCACGATGTCCGAAGACAAGAAGAAGCGCCTAT      780
  S  W  K  M  L  R  D  D  D  L  V  L  E  F  D  P  S  I  E
TGTCGTGGTGGAAGATGCTCCGCGACGACTTAGTGCTCGAGTTCGACCCATCCAACG         840
  P  Y  E  G  M  A  G  G  F  R  Y  V  P  R  G  I  E  D  D
AGCCCTACGAAGGTATGGTCGGGGGGTTCAGGTACGTCCCCCCGAGGCATCGAGGATG        900
  D  L  L  I  R  V  N  E  H  T  N  L  T  A  E  G  E  L  L  W
ACGATCTCCTGATCCGGGTGAACGAGCACACCAACCTCACCGCCGAGGGTGAACTCCTCT      960
  S  W  P  D  D  I  E  E  L  L  S  E  P  *
GGTCGTGGCCAGACGACATCGAGGAGCTTCTCTCGGAGCCCTAAAAGTCACGACCGGTTG     1020
TGTGAGCCAACCCAGGCCCGCGCAACGAAAGGAAACCCCTGCCCCTCACTCGGCTCGCAA     1080
AGCTGTTCGTAGACAACCTCGTCCACACTCACCGCAAGTCATCGCCGATCATCCAGGGT     1140
GGCTGTTCGCGCAGAGGTGTGAGGCGTGGAAGGCCAACTGGACGAAGACCCAGTCT        1200
CAGTTCTGCTCGTCTACCGCCAGTCCTCGTGTAAAAGACACCTCACGACTTTATCGGCCTG   1260
TGTCGAATTTGATTCTTTCCGGAACAAAGTCGAGTACGTA                         1320
``` pGH 15
3875 base pairs
Sites <= 2

AlwNI 2406

298 AvaI
404 DraIII
407 BsaAI
510 NaeI

707 BbeI
707 NarI
717 BglI
728 FspI
748 PvuI
778 PvuII

868 EcoRI
874 SacI
880 Asp 718
880 KpnI
915 AlwNI
936 ClaI
954 BstXI
1005 BamHI
1026 BbvII
1136 BspMI
1201 NdeI
1295 MscI
1437 BsmI
1446 XcmI
1580 BstXI
1610 StyI
1618 AccI
1618 HinCII
1618 <u>SalI</u>
1622 BspMI
1624 PstI
1630 SphI
1636 HinDIII
1817 PvuII

| | |
|---|---|
| | 404 DraIII |
| | 407 BsaAI |
| | 510 NaeI |
| | 707 BbeI |
| | 707 NarI |
| | 728 FspI |
| | 748 PvuI |
| | 868 EcoRI |
| | 987 EcoRI |
| | 993 SacI |
| | 999 Asp718 |
| | 999 KpnI |
| AatII 6330 | 1188 PflMI |
| XmnI 6007 | 1338 NsiI |
| ScaI 5890 | 1537 EcoNI |
| FspI 5632 | 1578 SmaI |
| GsuI 5497 | 1604 NsiI |
| HgiEII 5100 | 1795 NruI |
| | 1852 PaoR71 |
| AflIII 4519 | 1852 XhoI |
| PvuII 4341 | 2153 BbvII |
| HinDIII 4160 | 2190 HinCII |
| SphI 4154 | 2223 PstI |
| PstI 4148 | 2349 GsuI |
| SalI 4142 | 2533 NaeI |
| HinCII 4142 | 2537 SphI |
| AccI 4142 | 2658 Bsu36I |
| XcmI 3970 | 2670 Tth111I |
| MscI 3819 | 2686 BglII |
| NdeI 3725 | 2813 DsaI |
| BbvII 3550 | 2934 SplI |
| KpnI 3404 | 2951 ApaI |
| Asp718 3404 | 2969 BstEII |
| MscI 3226 | 3048 EagI |
| | 3118 XcmI |
| | 3153 AvrII |

PM1133
6399 base pairs
Sites <=2 res, attP, res, int, Kan^R

FIG. 37
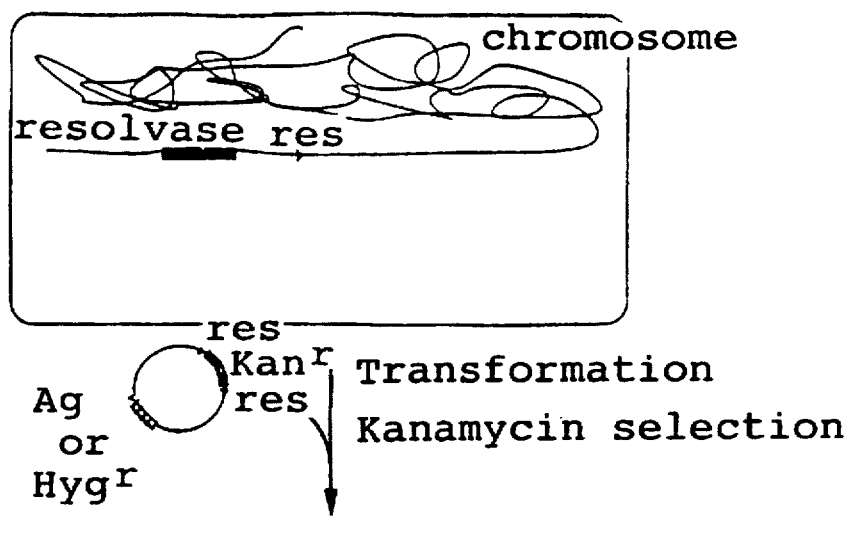
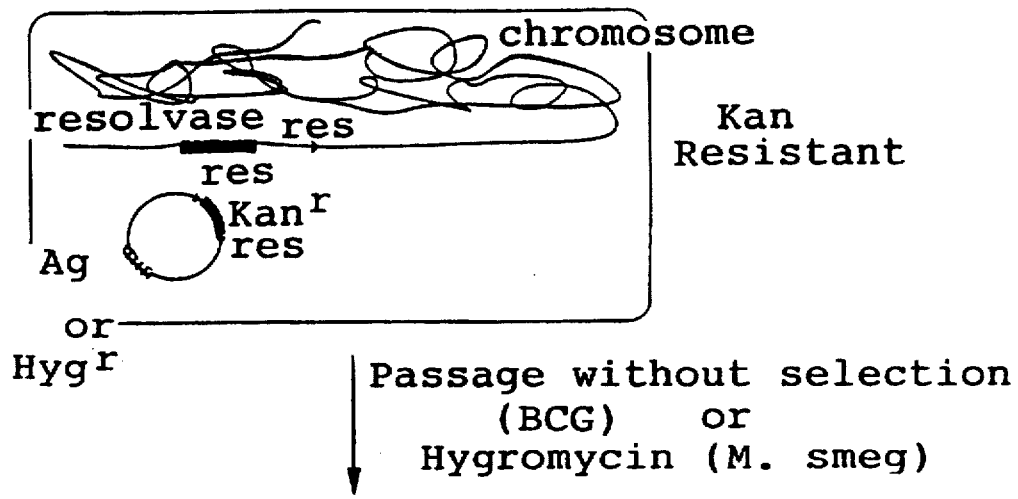
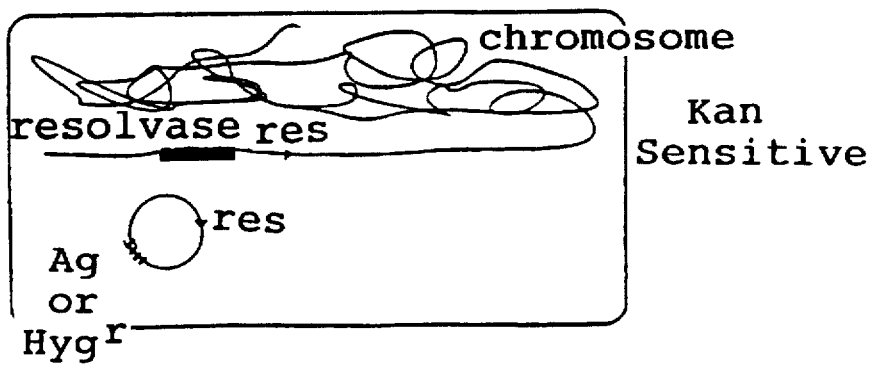

pSLH 231

Digestion with EcoR I

| Unresolved | Resolved |
|---|---|
| 4,816 bp | 3,473 bp |
| 1,312 bp | 1,312 bp | pSLH 231

Digestion with Xho I

| Unresolved | Resolved |
|---|---|
| 3,730 bp | 4,785 bp |
| 2,398 bp | | primary antibody: Rabbit anti OspA
secondary antibody: Goat anti Rabbit-HRP
Detection with ECL regent (Amersham)

VECTORS AND PROKARYOTES WHICH AUTOCATALYTICALLY DELETE ANTIBIOTIC RESISTANCE

This application is a continuation-in-part of U.S. application Ser. No. 07/861,002, filed on Mar. 31, 1992 and which is copending herewith.

This invention relates to the field of vectors and prokaryotes, such as bacteria and in particular to mycobacteria, transformed therewith, particularly as they are useful as vaccines. More particularly, this invention relates to prokaryotes which have been transformed with DNA from which antibiotic resistance traits are removed.

Certain mycobacteria represent major pathogens of man and animals. For example, tuberculosis is generally caused in humans by *Mycobacterium tuberculosis*, and in cattle by *Mycobacterium bovis*, which may also be transmitted to humans and other animals. *Mycobacteria leprae* is the causative agent of leprosy. *M. tuberculosis* and mycobacteria of the avium-intracellulare-scrofulaceum group (MAIS group) represent major opportunistic pathogens of patients with acquired immune deficiency syndrome (AIDS). *M. pseudotuberculosis* is a major pathogen of cattle.

On the other hand, Bacille Calmette-Guerin, or BCG, an avirulent strain of *M. bovis*, is widely used in human vaccines, and in particular is used as a live vaccine, which is protective against tuberculosis. BCG is the only childhood vaccine which is currently given at birth, has a very low incidence of adverse effects, and can be used repeatedly in an individual (e.g., in multiple forms). In addition, BCG and other mycobacteria (e.g., *M. smegmatis*), employed in vaccines, have adjuvant properties among the best currently known and, therefore, stimulate a recipient's immune system to respond to antigens with great effectiveness.

It has been suggested by Jacobs et al., *Nature*, 327: (6122): 532-535 (Jun. 11, 1987) that BCG could be used as a host for the construction of recombinant vaccines. In other words, it was suggested to take an existing vaccine (in this case against tuberculosis) and expand its protective repetoire through the introduction of one or more genes from other pathogens. Because BCG vaccines are administered as live bacteria, it is essential that any foreign antigens, polypeptides, or proteins expressed by the bacteria are not lost from the bacteria subsequent to vaccination.

Transformation, the process whereby naked DNA is introduced into bacterial cells, has been carried out successfully in mycobacteria. Jacobs et al. (1987), hereinabove cited, have described transformation of mycobacteria through chemical methods, and Snapper et al., *PNAS*, 85:6987-6991 (September 1988) have described transformation of mycobacteria by electroporation. Electroporation can give from $10^5$ to $10^6$ transformants per µg of plasmid DNA and such plasmid DNA's may carry genes for resistance to antibiotic markers such as kanamycin (Snapper, et al 1988) to allow for selection of transformed cells from non-transformed cells.

Jacobs et al. (1987) and Snapper et al. (1988) have also described the use of cloning vehicles, such as plasmids and bacteriophages, for carrying genes of interest into mycobacteria.

Combination of the above-mentioned techniques, along with standard tools of molecular cloning (e.g., use of restriction enzymes, etc.) allows the cloning of genes of interest into vectors and introduction of such genes into mycobacteria. To express these genes, it is important to have available signals for gene expression, in particular, transcription promoter elements. Such promoter elements have been isolated from mycobacterial heat shock genes, and used to express foreign antigens in mycobacteria.

There are, however, relatively few selectable markers for the transformation of mycobacteria and many of the antibiotic resistance methods that are useful for the fast-growing mycobacteria, such as, for example, *M. smegmatis*, are unsuitable for the slow-growing mycobacteria, such as *M. bovis* BCG, because many of the antibiotics themselves are not stable for the long periods of incubation required for growth of the organisms. In addition, the presence of antibiotic resistance genes in live bacterial vaccines, such as BCG vaccines, is undesirable because these genes may be transmitted to other bacteria present in the host, whereby such bacteria become resistant to the antibiotic.

It is therefore an object of the present invention to provide transformed prokaryotes, such as transformed mycobacteria, that do not retain antibiotic resistance genes used as selectable markers, and to provide vaccines employing such organisms.

Thus, in one aspect the invention provides a vector comprising a nucleotide sequence encoding an antibiotic resistance phenotype flanked by res sites. This vector can further comprise a nucleotide sequence encoding an attP site and a nucleic acid sequence encoding integrase. The vector can further comprise a nucleotide sequence encoding resolvase, particularly γδresolvase. Preferably this vector also comprises a promoter controlling the transcription of the resolvase coding sequence, particularly a mycobacterial promoter such as a heat shock promoter. For use in the production of a vaccine, for example, the vector can further comprise a nucleotide sequence encoding a heterologous antigen. In a particularly preferred embodiment of this aspect the vector comprises nucleotide sequences encoding an attP site, integrase and resolvase.

Another related aspect of the invention provides a prokaryote transformed with the above vector and which expresses resolvase. Preferably the prokaryote is a mycobacterium and preferably has an attB site-containing chromosome. Particulary preferred are mycobacteria selected from the group consisting of *Mycobacterium bovis*-BCG, *M. smegmatis, M. avium, M. phlei, M. fortuitum, M. lufu, M. paratuberculosis, M. habana, M. scrofalaceum, M. leprae*, and *M. intracellulare*.

In another embodiment of this aspect, the prokaryote expresses γδresolvase, and is again preferably a mycobacterium, particularly one which has an attB site-containing chromosome. The above-identified group of mycobacteria are particularly preferred. This embodiment particularly contemplates a mycobacterium integrated with a vector comprising nucleotide sequences encoding an attP site, integrase and resolvase.

Another embodiment of this aspect provides a mycobacterium integrated with a vector comprising nucleotide sequences encoding an attP site, integrase and resolvase and which is further transformed with an extrachromosomal vector comprising a nucleotide sequence encoding an antibiotic resistance phenotype flanked by res sites. The above-identified group of specific mycobacteria are also preferred in this embodiment.

In accordance with another aspect of the present invention, there is provided a prokaryote transformed with DNA which includes at least one DNA sequence which encodes immunity to a lytic bacteriophage.

FIG. 5 illustrates the 9.5 kb KpnI fragment described in Example 1.

FIG. 6 shows the nucleotide sequence of a 1.3 kb subsequent of the above 9.5 kb KpnI fragment and the 183 amino acid encoded thereby.

FIG. 37 illustrates the strategy for deleting an antibiotic resistance gene flanked by res sites from an integrating vector using a resolvase gene present in trans in the transformed host's chromosome.

Figure 1:
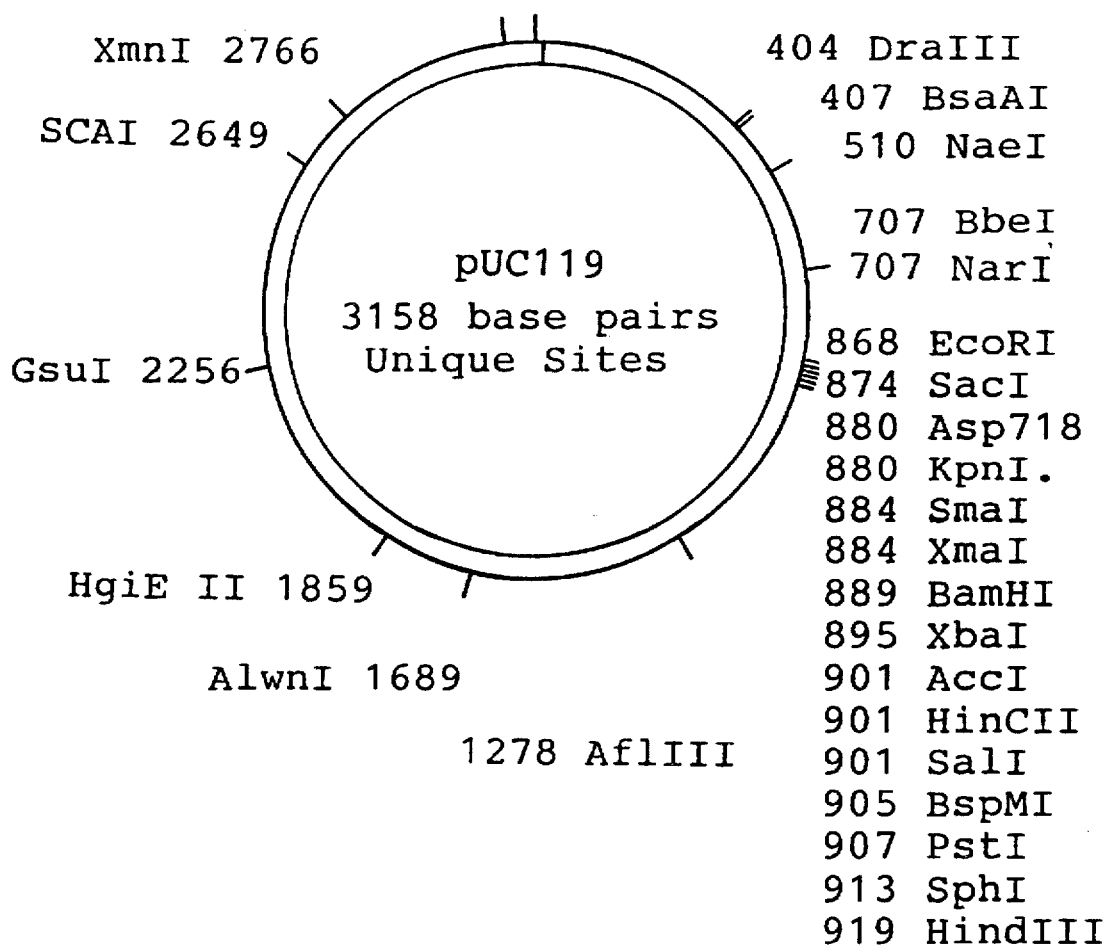
FIG. 1 illustrates the plasmid pVC119 described in Example 1.

Prokaryotes which may be transformed with DNA which includes at least one DNA sequence which encodes immunity to a lytic bacteriophage include, but are not limited to, bacteria. Bacteria which may be transformed include, but are not limited to, mycobacteria, Actinomyces species, Norcardia species, Streptomyces species, Corynebacteria species, Salmonella species, Vibrio species, and E. coli. In one embodiment, the bacterium is a mycobacterium. Mycobacteria which may be transformed include, but are not limited to, Mycobacterium bovis-BCG, M. smegmatis, M. avium, M. phlei, M. fortiutum, M. lufu, M. paratuberculosis, M. habana, M. scrofalaceum, M. leprae, and M. intracellulare. In one embodiment, the mycobacterium is M. bovis-BCG. In another embodiment, the mycobacterium is M. smegmatis.

As hereinabove stated, the prokaryote is transformed with DNA which includes at least one DNA sequence which encodes immunity to a lytic bacteriophage. Temperate bacteriophages can adopt two different life cycles. The lytic cycle involves simple reproduction of viral particles within a bacterial cell, followed by lysis of the cell and release of the particles. Alternatively, temperate phages enter a lysogenic state in which most of the viral functions are inactivated, and the phage genome becomes integrated into the bacterial chromosome. The lytic functions of the phage are inactivated by a transcriptional repressor. The repressor regulates the genes of the resident prophage, and also prevents the lytic cycles of any superinfecting phages, thereby conferring immunity to a lytic bacteriophage.

In one embodiment, the at least one DNA sequence encodes immunity to a lytic mycobacteriophage. As an illustrative example, mycobacteriophage L5 is a temperate phage that infects and lysogenizes M. smegmatis. In accord with the temperate nature of L5, it not only infects M. smegmatis but also forms stable lysogens in which the bacteriophage genome is integrated into the bacterial chromosome and the lyric functions have been inactivated (Snapper et al., *Proc. Nat. Acad. Sci.*, 85:6987–6991, 1988, and Lee et al., *Proc. Nat. Acad. Sci.*, 88:3111–3115, 1991). L5 lysogens of *M. smegmatis* are immune to superinfection by L5, and also to superinfection by another mycobacteriophage known as mycobacteriophage D29. Mycobacteriophage D29, however, is not a temperate phage and does not itself form lysogens.

A gene has been isolated from the L5 genome, which encodes a 183 amino acid protein, which confers immunity to L5 superinfection. This gene, which is approximately 0.6 kb in length, is designated gene 71. As further described hereinbelow, this gene has been placed into an *E. coli* mycobacteria shuttle vector. The vector was then electroporated into *M. smegmatis*. Transformants were then selected by infection with bacteriophage L5c(d1), which is a variant of L5 that does not lysogenize. Therefore, the *M. smegmatis* organisms which have been transformed with the shuttle vector will survive the L5c(d1) infection. It is to be understood, however, that the scope of the present invention is not to be limited to immunity to L5 or any other mycobacteriophage superinfection, or to any specific genes which encode mycobacteriophage immunity, such as gene 71 of L5.

In one embodiment, the DNA which transforms the mycobacterium includes a first DNA sequence which is a phage DNA portion encoding bacteriophage integration, preferably mycobacteriophage integration, into a mycobacterium chromosome, and the at least one DNA sequence which encodes immunity to a lytic bacteriophage.

The term "phage DNA portion", as used herein, means that the DNA sequence is derived from a phage and lacks the DNA which is required for phage replication.

Bacteriophages from which the phage DNA portion may be derived include, but are not limited to, mycobacteriophages, such as but not limited to the L5, L1, Bxb1 and TM4 mycobacteriophages; the lambda phage of *E.coli*; the toxin phages of Corynebacteria; phages of Actinomycetes and Nocardia, the O/C31 phage of Streptomyces; and the P22 phage of Salmonella. Preferably, the phage DNA portion encodes mycobacteriophage integration into a mycobacterium chromosome.

In a preferred embodiment, the first DNA sequence includes DNA encoding integrase, which is a protein that provides for integration of the DNA into the mycobacterial chromosome. Most preferably, the first DNA sequence also includes DNA which encodes an AttP site.

The DNA sequence encoding the AttP site and the integrase provides for an integration event which is referred to as site-specific integration. DNA containing the AttP site and the integrase gene is capable of integration into a corresponding AttB site of a mycobacterium chromosome.

It is to be understood that the exact DNA sequence encoding the attP site may vary among different phages, and that the exact DNA sequence encoding the attB site may vary among different mycobacteria.

The integration event results in the formation of two new junction sites called AttL and AttR, each of which contain part of each of AttP and AttB. The inserted and integrated DNA which includes the first DNA sequence and the DNA which encodes immunity to a lytic bacteriophage, is flanked by the AttL and AttR sites. The insertion and integration of the phage DNA portion results in the formation of a transformed mycobacterium.

The DNA may further include a DNA sequence encoding a protein or polypepetide heterlogous to the mycobacterium into which the DNA is to be integrated.

The DNA which encodes a protein heterologous to mycobacteria may be DNA which is all or a portion of a gene encoding protein(s) or polypeptide(s) of interest; DNA encoding a selectable marker or markers; or DNA encoding both a selectable marker or markers and at least one protein or polypeptide of interest.

Protein(s) or polypeptide(s) of interest, which may be encoded by such DNA include, but are not limited to, antigens, anti-tumor agents, enzymes, lymphokines, pharmacologic agents, immunopotentiators, and reporter molecules of interest in a diagnostic context.

Antigens for which such DNA sequence may encode include, but are not limited to, *Mycobacterium leprae* antigens; *Mycobacterium tuberculosis* antigens; Rickettsia antigens; malaria sporozoites and merozoites; diphtheria toxoids; tetanus toxoids; Clostridium antigens; Leishmania antigens; Salmonella antigens; Borrelia antigens; *Mycobacterium africanum* antigens; *Mycobacterium intracellulare* antigens; *Mycobacterium avium* antigens; Treponema antigens; Pertussis antigens; Schistosoma antigens; Filaria antigens; Herpes virus antigens; influenza and parainfluenza virus antigens; measles virus antigens; mumps virus antigens; hepatitis virus antigens; Shigella antigens; Neisseria antigens; rabies antigens, polio virus antigens; Rift Valley Fever virus antigens; dengue virus antigens; measles virus antigens; Human Immunodeficiency Virus (HIV) antigens; respiratory syncytial virus (RSV) antigens; snake venom antigens; and *Vibrio cholera* antigens. Enzymes which may be encoded include, but are not limited to, steroid enzymes.

Anti-tumor agents which may be encoded by such DNA include, but are not limited to, interferon-α, interferon-β, or interferon-γ, and tumor necrosis factor, or TNF. Lymphokines which may be encoded include, but are not limited to, interleukins 1 through 8.

Reporter molecules which may be encoded include, but are not limited to, luciferase, β-galactosidase, β-glucuronidase, and catechol dehydrogenase.

Other peptides or proteins which may be encoded by such DNA sequence include, but are not limited to, those which encode for stress proteins, which can be administered to evoke an immune response or to induce tolerance in an autoimmune disease (eg., rheumatoid arthritis).

The phage DNA portion of the present invention, which includes the first DNA sequence encoding mycobacterium phage integration into a mycobacterium chromosome, the at least one DNA sequence encoding immunity to a lytic bacteriophage; and the DNA encoding at least one protein or polypeptide heterologous to mycobacteria, may be constructed through genetic engineering techniques known to those skilled in the art. In a preferred embodiment, the phage DNA portion may be a plasmid including, in addition to the DNA encoding integration and the DNA encoding a heterologous protein, an origin of replication for any of a wide variety of organisms, which includes, but is not limited to, *E.coli*, Streptomyces species, Bacillus species, Staphylococcus species, Shigella species, Salmonella species and various species of *pneumococci*. Most preferably, the plasmid includes an origin of replication for *E.coli*.

The phage DNA portion also may include a suitable promoter for controlling expression of the at least one DNA sequence encoding a protein or polypeptide heterologous to the mycobacterium. Suitable promoters include, but are not limited to, mycobacterial promoters such as the BCG HSP60 and HSP70 promoters; mycobactin promoters of *M. tuberculosis* and BCG, the superoxide dismutase promoter, the α-antigen promoter of *M. tuberculosis* and BCG, the MBP-70 promoter, the 45 kda antigen promoter of *M. tuberculosis* and BCG; and the mycobacterial asd promoter; the mycobacterial 14 kda and 12 kda antigen promoters; mycobacteriophage promoters such as the Bxb1 promoter, the L1, L5, and D29 promoters, and the TM4 promoters; *E.coli* promoters; or any other suitable promoter. The selection of a suitable promoter is deemed to be within the scope of those of ordinary skill in the art from the teachings contained herein.

The promoter sequence may, in one embodiment, be part of an expression cassette which also includes a portion of the gene normally under the control of the promoter. For example, when a mycobacterial HSP60 or HSP70 promoter is employed, the expression cassette may include, in addition to the promoter, a portion of the gene for the HSP60 or HSP70 protein. When the expression cassette and the at least one DNA sequence encoding a protein or polypeptide heterologous to the mycobacterium such as hereinabove described, are expressed, the protein expressed by the cassette and the DNA encoding a protein or poplypeptide heterologous to the mycobacterium is a fusion protein of a fragment of a mycobacterial protein (eg., the HSP60 or HSP70 protein), and the protein or polypeptide heterologous to the mycobacterium.

In a preferred embodiment, the transcription initiation site, the ribosomal binding site, and the start codon, which provides for the initiation of the translation of mRNA, are each of mycobacterial origin. The stop codon, which stops translation of mRNA, thereby terminating synthesis of the protein or peptide heterologous to the mycobacterium, and the transcription termination site, may be of mycobacterial origin, or of other bacterial origin, or such stop codon and transcription termination site may be those of the at least one DNA sequence encoding a protein or polypeptide heterologous to the mycobacterium.

In accordance with another embodiment, the mycobacterium is transformed with an expression vector including the at least one DNA sequence which encodes immunity to a bacteriophage, and a promoter selected from the class consisting of mycobacterial promoters and mycobacteriophage promoters for controlling expression of at least one DNA sequence encoding a protein or polypeptide heterologous to the mycobaterium. The mycobacterial and mycobacteriophage promoters and heterologous proteins and polypeptides may be selected from those hereinabove described.

The promoter sequence may also be part of an expression cassette which also includes a portion of the gene normally under the control of the promoter, as hereinabove described. When the expression cassette and the at least one DNA sequence encoding a protein or polypeptide heterologous to the mycobacterium, are expressed, the protein expressed by the cassette and the at least one DNA sequence is a fusion protein of a fragment of a mycobacterial protein and the protein or polypeptide heterologous to the mycobacterium.

Also as hereinabove described, the transcription initiation site, the ribosomal binding site, and the start codon, which provides for the initiation of the translation of mRNA, may each be of mycobacterial origin. The stop codon, may, as hereinabove described, be of mycobacterial origin, or of other bacterial origin, or such stop codon and transcription termination site may be those of the DNA encoding the at least one protein or polypeptide heterologous to the mycobacterium.

In accordance with one embodiment, the vector further includes a mycobacterial origin of replication.

In accordance with another embodiment, the vector may be a plasmid. The plasmid may be a non-shuttle plasmid, or may be a shuttle plasmid which further includes a bacterial origin of replication such as an *E. coli* origin of replication, a Bacillus origin of replication, a Staphylococcus origin of replication, a Streptomyces origin of replication, or a pneumococcal origin of replication. In one embodiment, the shuttle plasmid includes an *E. coli* origin of replication.

In accordance with yet another embodiment, the vector may further include a multiple cloning site, and the at least one DNA encoding a protein or polypeptide heterologous to the mycobacterium sequence is inserted in the multiple cloning site.

In addition to the DNA encoding immunity to a lytic bacteriophage, DNA encoding a heterlogous protein or polypeptide, and the mycobacterial promoter for controlling expression of the at least one DNA sequence encoding a heterologous protein or polypeptide, the expression vector may, in one embodiment, further include a DNA sequence encoding bacteriophage integration into a mycobacterium chromosome. Bacteriophages from which the DNA sequence encoding bacteriophage integration into a mycobacterium chromosome may be derived include, but are not limited to, those hereinabove described. Preferably, the DNA sequence encodes mycobacteriophage integration into a mycobacterium chromosome. The DNA sequence which encodes bacteriophage integration into a mycobacterium chromosome may include DNA which encodes integrase, which is a protein that provides for integration of the vector into the mycobacterial chromosome. Preferably, the DNA sequence encoding mycobacteriophage integration also includes DNA which encodes an attP site.

The DNA encoding the attP site and the integrase provides for an integration event which is referred to as site-specific integration. DNA containing the attP site and the integrase gene is capable of integrating into a corresponding attB site of a mycobacterium chromosome, as hereinabove described.

It is to be understood that the exact DNA sequence encoding the attP site may vary among different phages, and that the exact DNA sequence encoding the attB site may vary among different mycobacteria.

The transformed mycobacteria, which include DNA which includes at least one DNA sequence which encodes immunity to a lytic bacteriophage, and preferably a DNA sequence which encodes a protein or polypeptide which is heterologous to mycobacteria, may be utilized in the production of a vaccine or a therapeutic agent, depending upon the protein(s) or polypeptide expressed by the transformed mycobacteria.

To form such a vaccine or therapeutic agent, the transformed mycobacteria are administered in conjunction with a suitable pharmaceutical carrier. As representative examples of suitable carriers there may be mentioned: mineral oil, alum, synthetic polymers, etc. Vehicles for vaccines and therapeutic agents are well known in the art and the selection of a suitable vehicle is deemed to be within the scope of those skilled in the art from the teachings contained herein. The selection of a suitable vehicle is also dependent upon the manner in which the vaccine or therapeutic agent is to be administered. The vaccine or therapeutic agent may be in the form of an injectable dose and may be administered intramuscularly, intravenously, orally, intradermally, or by subcutaneous administration.

Other means for administering the vaccine or therapeutic agent should be apparent to those skilled in the art from the teachings herein; accordingly, the scope of the invention is not to be limited to a particular delivery form.

When the transformed mycobacteria are employed as a vaccine, such a vaccine has important advantages over other presently available vaccines. Mycobacteria have, as hereinabove indicated, adjuvant properties among the best currently known and, therefore, stimulate a recipient's immune system to respond with great effectiveness. This aspect of the vaccine induces cell-mediated immunity and thus is especially useful in providing immunity against pathogens in cases where cell-mediated immunity appears to be critical for resistance. Also, mycobacteria may stimulate long-term memory or immunity. It thus may be possible to prime long-lasting T cell memory, which stimulates secondary antibody responses neutralizing to the infectious agent or the toxin. Such priming of T cell memory is useful, for example, against tetanus and diphtheria toxins, pertussis, malaria, influenza virus, Herpes virus, rabies, Rift Valley fever virus, dengue virus, measles virus, Human Immunodeficiency Virus (HIV), respiratory syncytial virus, human tumors, and snake venoms. Another advantage in employing mycobacteria transformed with the phage DNA portion of the present invention as a vaccine or a therapeutic agent is that mycobacteria in general have a large genome (i.e., approximately $3 \times 10^6$ base pairs in length). Because the genome is large, it is able to accommodate a large amount of DNA from other source(s), and may possibly be employed to make a vaccine and/or therapeutic agent containing DNA sequences encoding more than one antigen and/or therapeutic agent.

As hereinabove stated, it is desired that antibiotic markers be removed from the transformed mycobacteria prior to utilization of the mycobacteria in a vaccine. In one embodiment, a vector is constructed which includes an attP site, DNA encoding immunity to a bacteriophage, DNA encoding integrase, an antibiotic resistance marker, and directly oriented copies of a site which may be recognized by a resolvase protein. An in vitro reaction using purified resolvase protein resolves the vector into a catenane which comprises two daughter molecules which are topologically linked as singly-linked circular DNA molecules. One circle includes the attP site and the DNA which encodes immunity to a lytic bacteriophage. The other circle includes the gene encoding integrase as well as the antibiotic resistance marker. This circle does not include a mycobacterial origin of replication. When the singly-linked circles are transformed into a mycobacterium, the circle containing the attP site and the gene encoding immunity to a lytic bacteriophage will integrate into the mycobacterial chromosome. The circle which includes the gene encoding integrase and the antibiotic resistance marker does not integrate into the mycobacterial chromosome. When the catenane is transfected into the mycobacterium, the catenane becomes a substrate for cellular DNA topoisomerase II enzyme. The action of the enzyme upon the catenane results in the separation of the two circular DNA molecules from each other. Although the integrase and the antibiotic resistance marker are expressed when the circular DNA molecules are first transfected into the mycobacterium, the circle which includes the antibiotic resistance marker will eventually be lost because such circle cannot integrate, nor can the circular DNA molecule replicate within the mycobacterium. Thus, there are provided transformed mycobacteria which do not include antibiotic resistance markers, and may be selected through bacteriophage infection.

Figure 30:
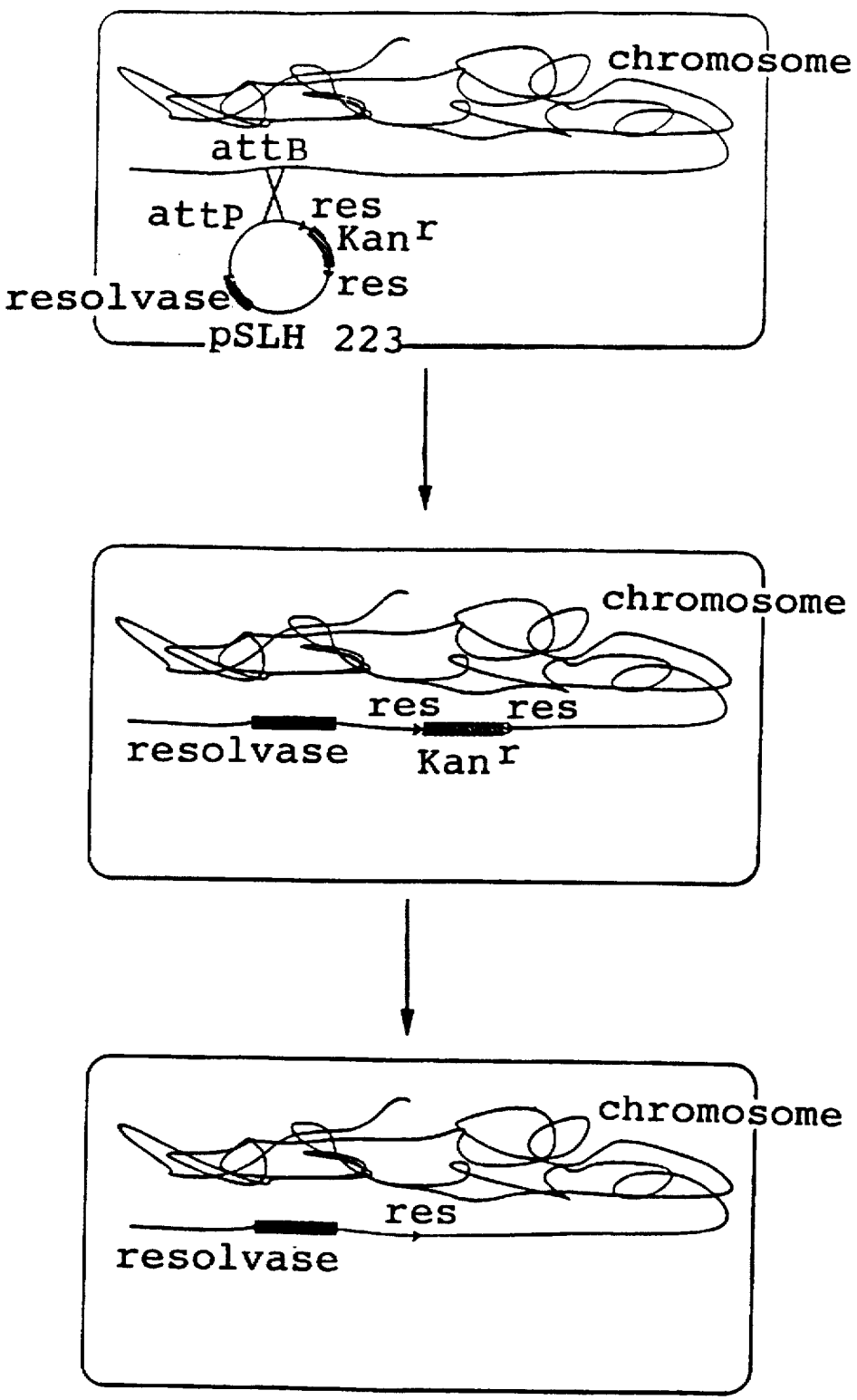
FIG. 30 illustrates the strategy for deleting an antibiotic resistance gene flanked by res sites from an integrating vector using a resolvase gene present in cis in the vector.
Figure 31:
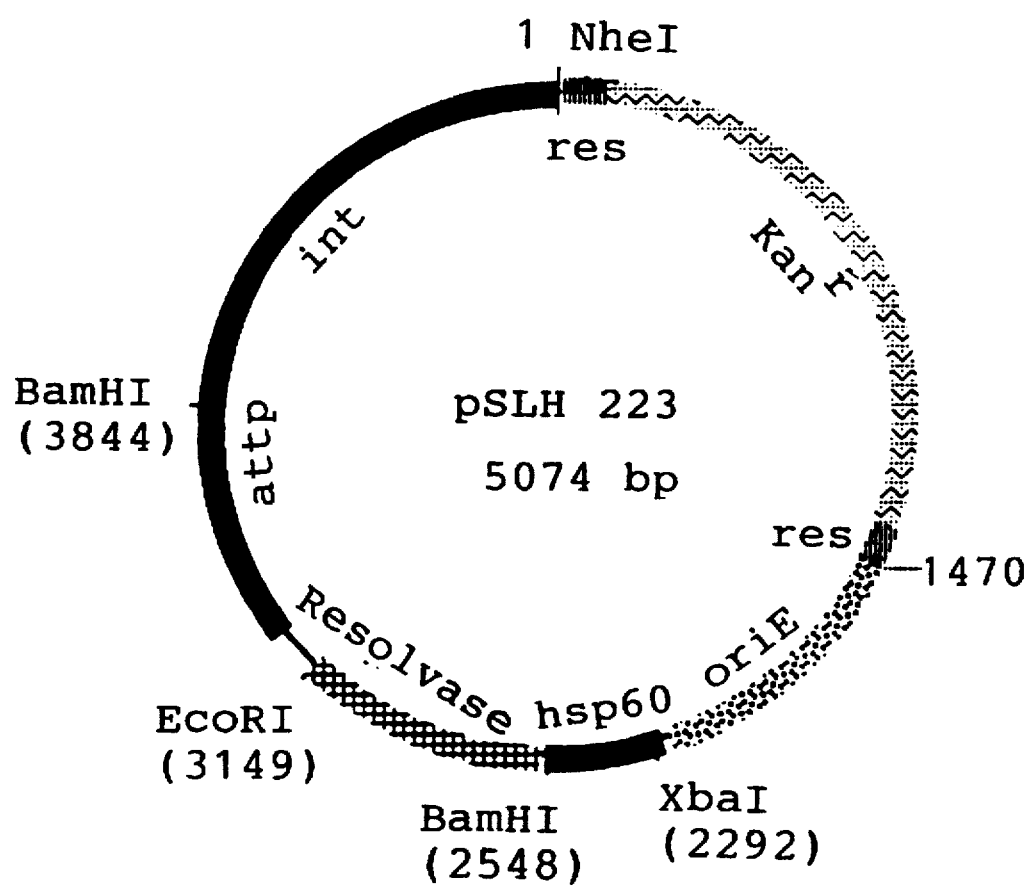
FIG. 31 illustrates the plasmid pSLH223 described in Example 6.
Figure 32:
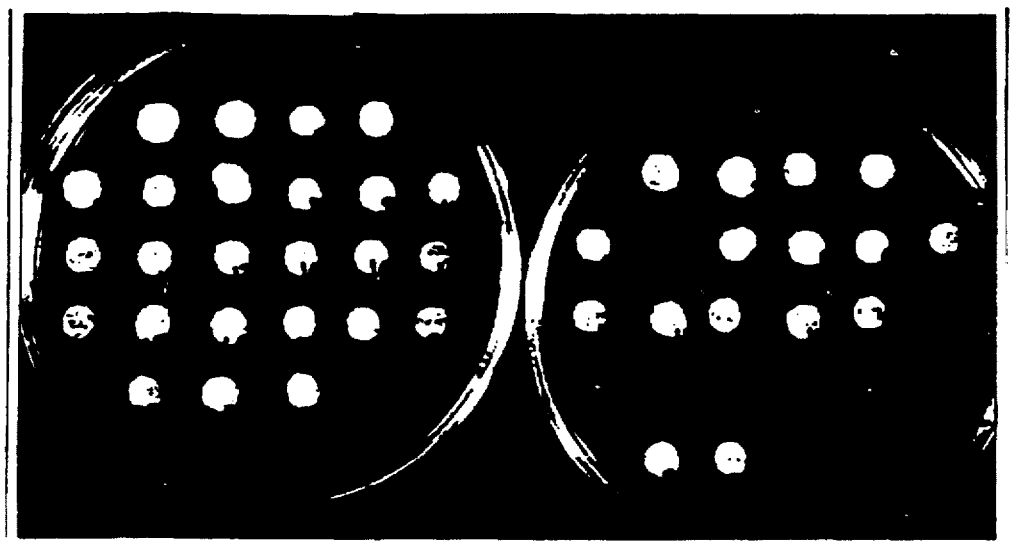
FIG. 32 shows cultures grown in the presence and absence of kanamycin to identify M. smegmatis:223 as described in Example 6.
Figure 33:
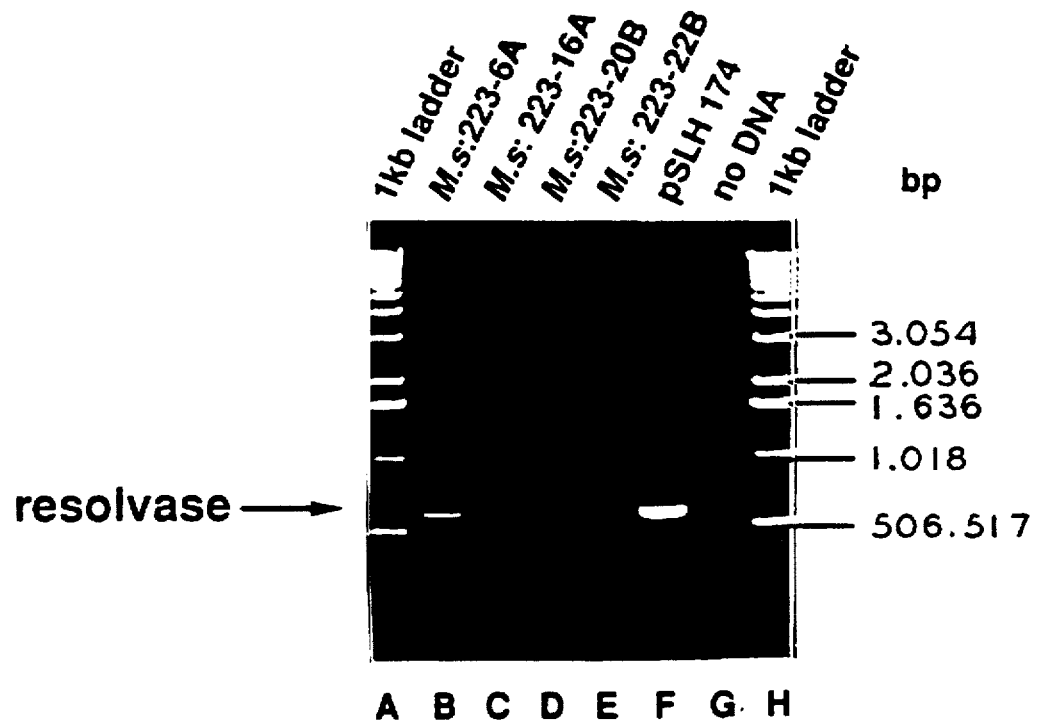
FIG. 33 shows ethidium bromide-stained agarose gel columns demonstrating the detection of the resolvase gene in M.smegmatis:223 as described in Example 6.
Figure 34:
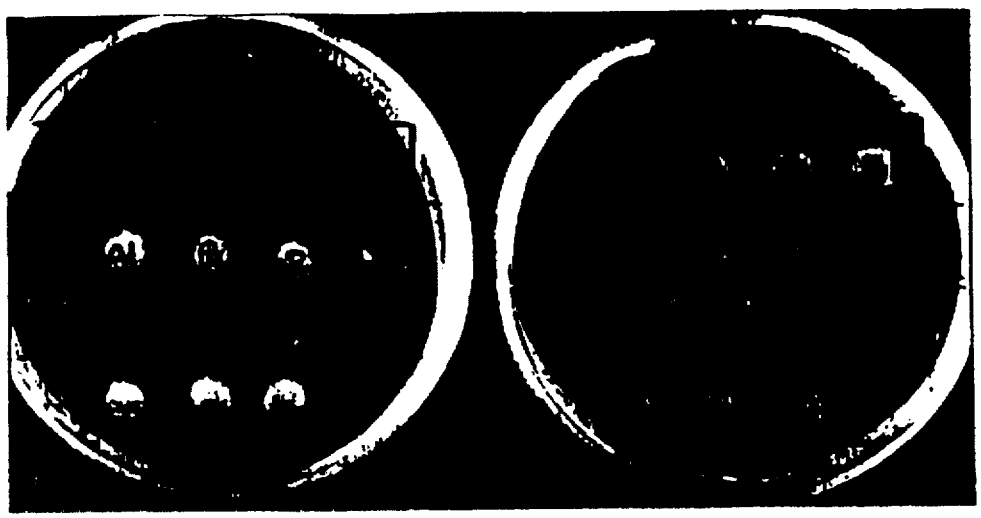
FIG. 34 shows cultures grown in the presence and absence of kanamycin to identify BCG:223 as described in Example 6.
Figure 35:
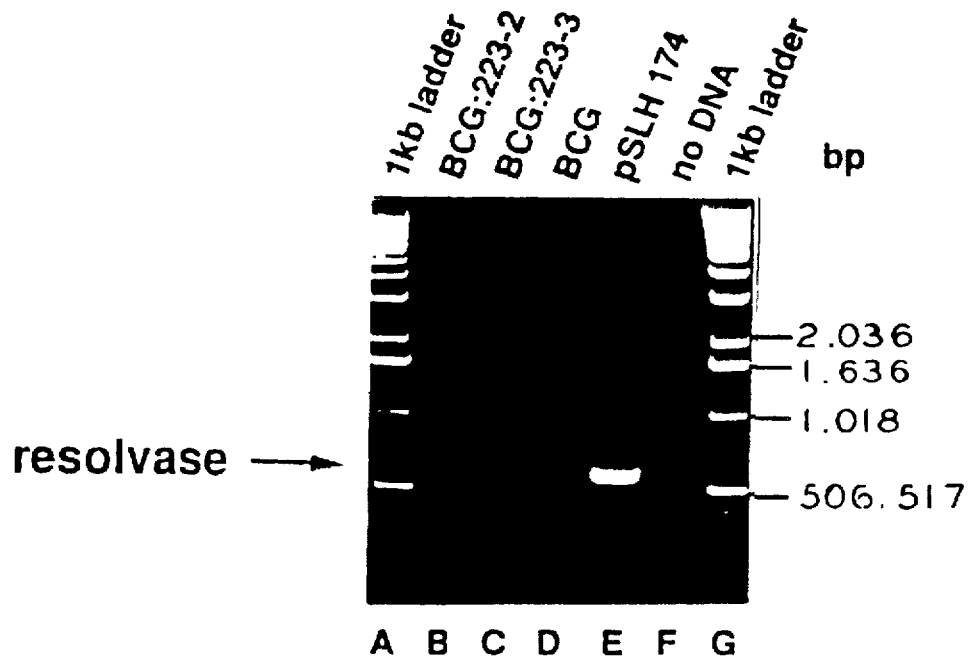
FIG. 35 shows ethidium bromide-stained agarose gel columns demonstrating the detection of the resolvase gene in BCG:223 as described in Example 6.
Figure 36:
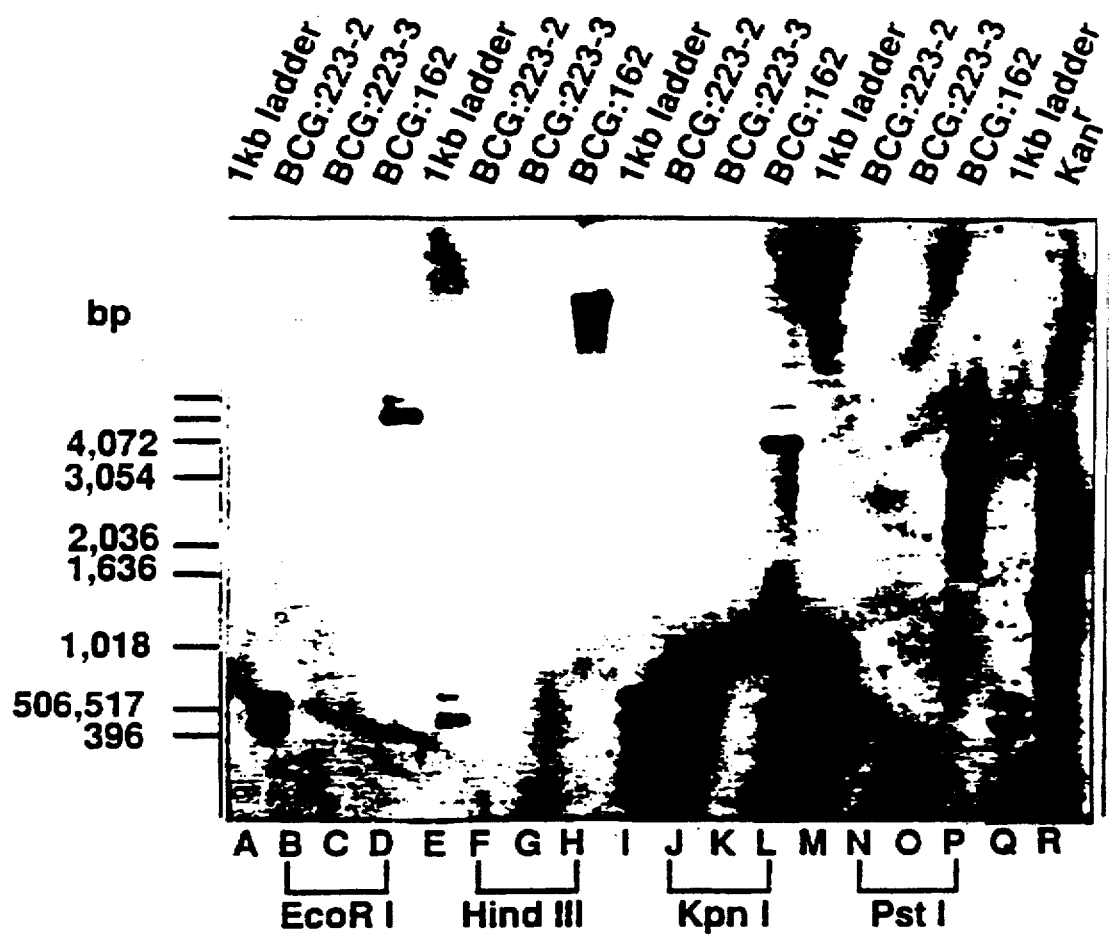
FIG. 36 shows the results of a Southern hybridization confirming the deletion of the $Kan^r$ gene in rBCG:223 as described in Example 6.
Figure 38:
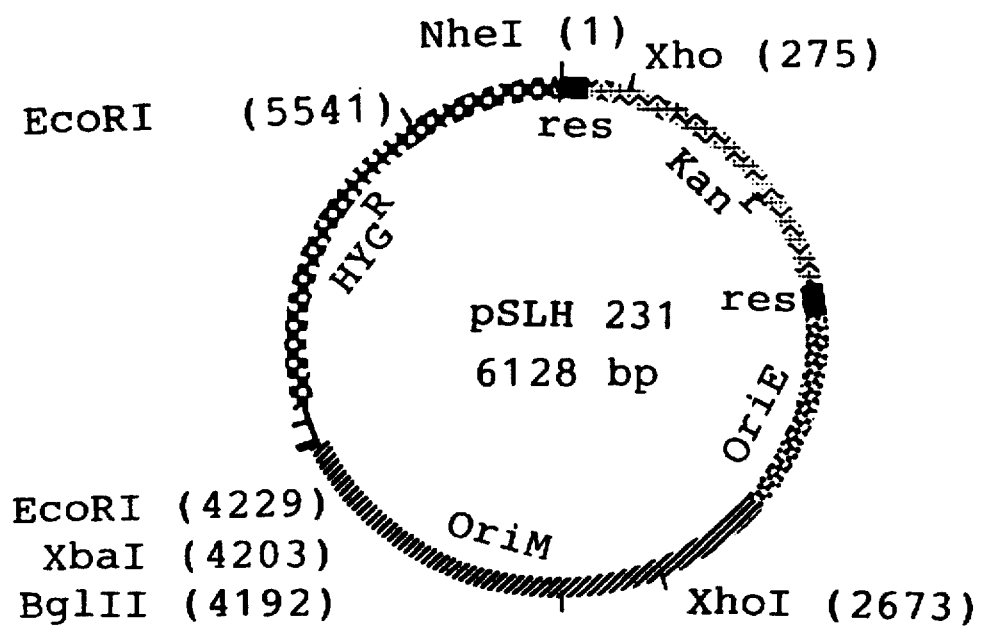
FIG. 38 illustrates the plasmid pSLH211 as described in Example 6.

FIG. 30 generally illustrates the autocatalytic deletion of an antibiotic resistance gene, e.g. $Kan^r$, gene in cis (on the same DNA element). An integrating vector was constructed that expresses resolvase under the control of a mycobacterial, e.g., BCG hsp60, promoter and contains the antibiotic resistance gene flanked by res sites, the substrate of resolvase activity. The plasmid also contains the attP-int locus of mycobacteriophage L5 for site specific attachment and unidirectional integration of the vector into the unique attB site of the mycobacterial (e.g. BCG or M. smegmatis) chromosome catalyzed by the int gene product (not shown). This recombination event is diagrammed at the top of FIG. 30. After transformation, initial selection of bacteria harboring the vector is made on plates containing the antibiotic corresponding to the resistance gene. The genomic structure of the resistant transformants is diagrammed in the middle of FIG. 30. Kanamycin resistant colonies are picked and then passaged without antibiotic selection. Resolvase acts on the res sites to excise the resistance gene, thereby deleting the antibiotic resistance marker. Release of antibiotic selection allows isolation of these antibiotic sensitive recombinants. The genomic structure of these antibiotic recombinants is diagramed at the bottom of FIG. 30.

Figure 39:
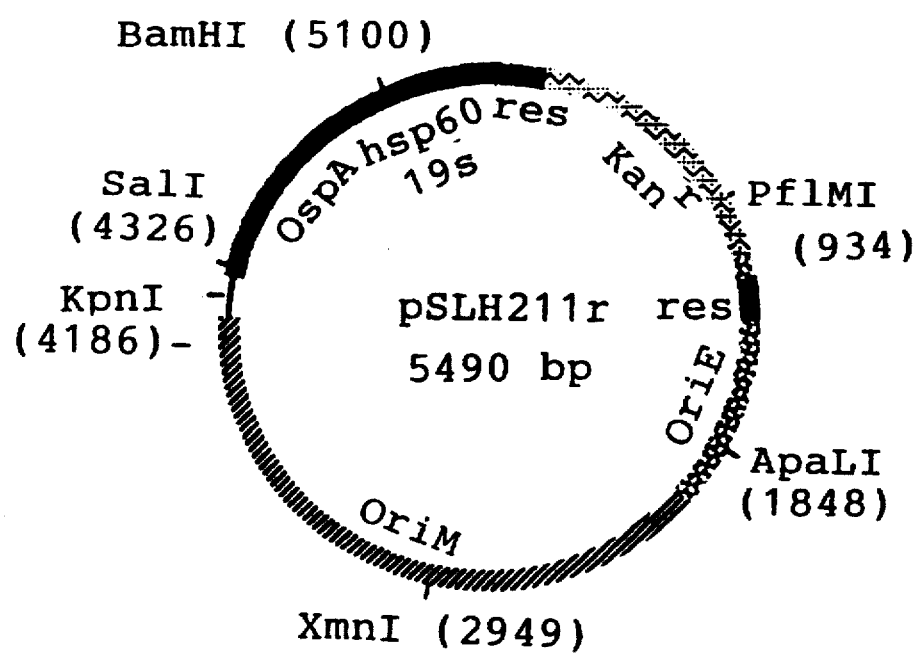
FIG. 39 illustrates the plasmid pSLH211r as described in Example 6.

FIG. 37 illustrates the flexibility of the res-resolvase system of the invention. This system promotes autocatalytic deletion of marker genes even when the targets of resolvase action (flanked by res sites) are on a different DNA element (active in trans) not just on the same DNA element as described with reference to FIG. 30. Resolvase expressed after stable host chromosomal integration of its gene can act in trans to remove an antibiotic resistance gene from extra-chromosomally replicating plasmids. For example, pSLH 231 (FIG. 39) was constructed and transformed into M. smegmatis:223 and pSLH 211r (FIG. 39) was constructed and transformed into BCG:223 (diagrammed at the top of FIG. 37). In addition to the $Kan^r$ gene flanked by res sites, these vectors contain a second marker gene. pSLH 231 contains a second resistance marker for hygromycin ($Hyg^r$), and pSLH 211r carries the gene for the antigen (Ag) OspA from Borrelia burgdorferi. The vectors pSLH and 211r do not integrate. After transformation, colonies were selected by growing in the presence of kanamycin. The genomic structure of these $Kan^r$ transformants is diagrammed in the middle of FIG. 37. M. smegmatis colonies were picked and passaged in media containing hydromycin, but without kanamycin. BCG transformants were picked and passaged without antibiotic selection. Resolvase acts on the res sites to excise the $Kan^r$ gene from the plasmids, thereby deleting this antibiotic resistance marker. The release of kanamycin selection allows isolation of $Kan^s$ recombinants. The genomic structure of these $Kan^s$ recombinants is diagrammed at the bottom of FIG. 37. The plasmid replicon is maintained in the cell for many generations in the absence of antibiotic selection allowing for confirmation of the presence of the second marker gene (Ag or $Hyg^r$). rBCG:223 pSLH 211rΔKan is one example of a BCG recombinant expressing a foreign antigen (OspA) and lacking a foreign antibiotic resistance gene.

Although the present invention has been described in detail with respect to mycobacteria, it is to be understood that within the scope of the present invention that prokaryotes other than mycobacteria may be transformed with the vector of the invention, and preferably also with DNA encoding a protein or polypeptide which is heterologous to the prokaryote.

The invention will now be described with respect to the following examples; however, the scope of the present invention is not intended to be limited thereby.

EXAMPLE 1

Mapping the Determinants of L5 Superimmunity

Figure 2:
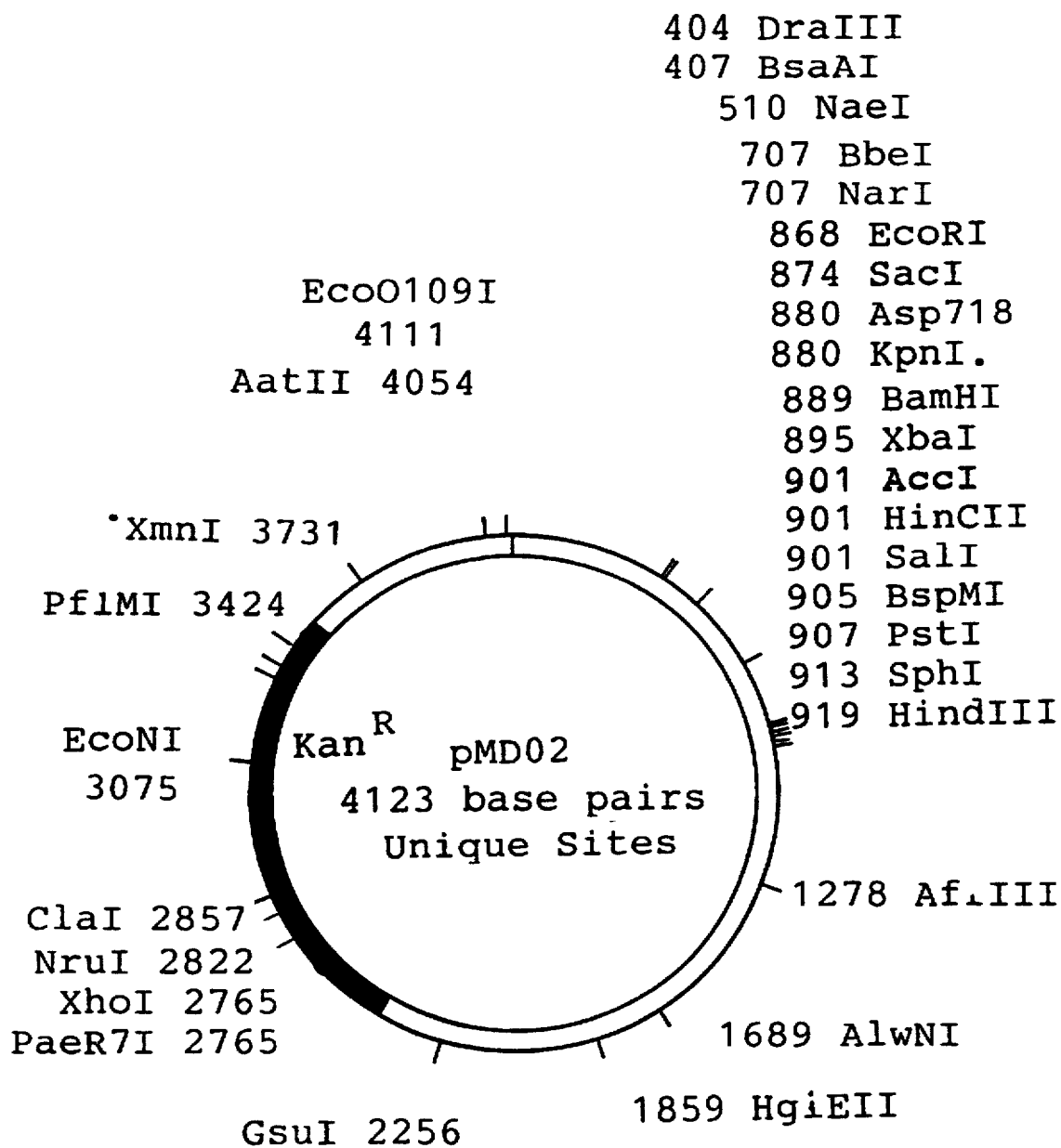
FIG. 2 illustrates the plasmid pMD02 described in Example 1.

Recombinant plasmids were constructed that contained segments of the mycobacteriophage L5 genome inserted into an E. coli-mycobacterial shuttle vector known as pMD30.

pMD30 is a derivative of pUC119 modified such that it may replicate in both *E. coli* and mycobacteria, and it contains the aph kanamycin resistance gene. pMD30 was constructed by inserting the 1 kb HindIII fragment from pKD43 (Derbyshire et al., *Proc. Nat. Acad. Sci.*, 84:8049–8053, (1987)) containing the aph gene into the ScaI site of pUC119 (FIG. 1) to make pMD02. (FIG. 2). pMD02 was then cleaved with XmnI and the HpaI-EcoRV fragment containing ori M from pYUB12 (FIG. 3, obtained from Dr. William Jacobs) was inserted. The resulting plasmid is pMD30 (FIG. 4). One recombinant plasmid, which contained a 9.5 kb KpnI fragment (FIG. 5), conferred immunity to L5 superinfection by wild-type L5 phage in *M. smegmatis*. Further analysis of this 9.5 kb KpnI fragment showed that a smaller segment, about 1.3 kb in length (FIG. 6), and including a gene encoding a 183 amino acid protein, conferred this phenotype, and that the 183 amino acid protein expressed by this 1.3 kb fragment was responsible. The gene encoding this 183 amino acid protein is referred to as gene 71. Gene 71 is located from nucleotide position 44,882 to nucleotide position 44,331 in the L5 genome.

EXAMPLE 2

Isolation of Clear Plaque Derivatives of L5

Clear plaque derivatives were isolated as spontaneous mutants that formed clear plaques on bacterial lawns, as opposed to the turbid plaques of the wild-type mycobacteriophage L5. Clear plaques indicate those cells which were killed by L5 infection and therefore cannot form lysogens. One of these derivatives, designated L5c(d1), was found to contain a small deletion of the L5 genome, including part of gene 71, by restriction enzyme digestion with Bgl II. Bacterial survivors of an L5c(d1) infection of *M. smegmatis* occur at a frequency of about $10^{-6}$.

EXAMPLE 3

A. Construction of Plasmids Including Gene 71

Figure 3:
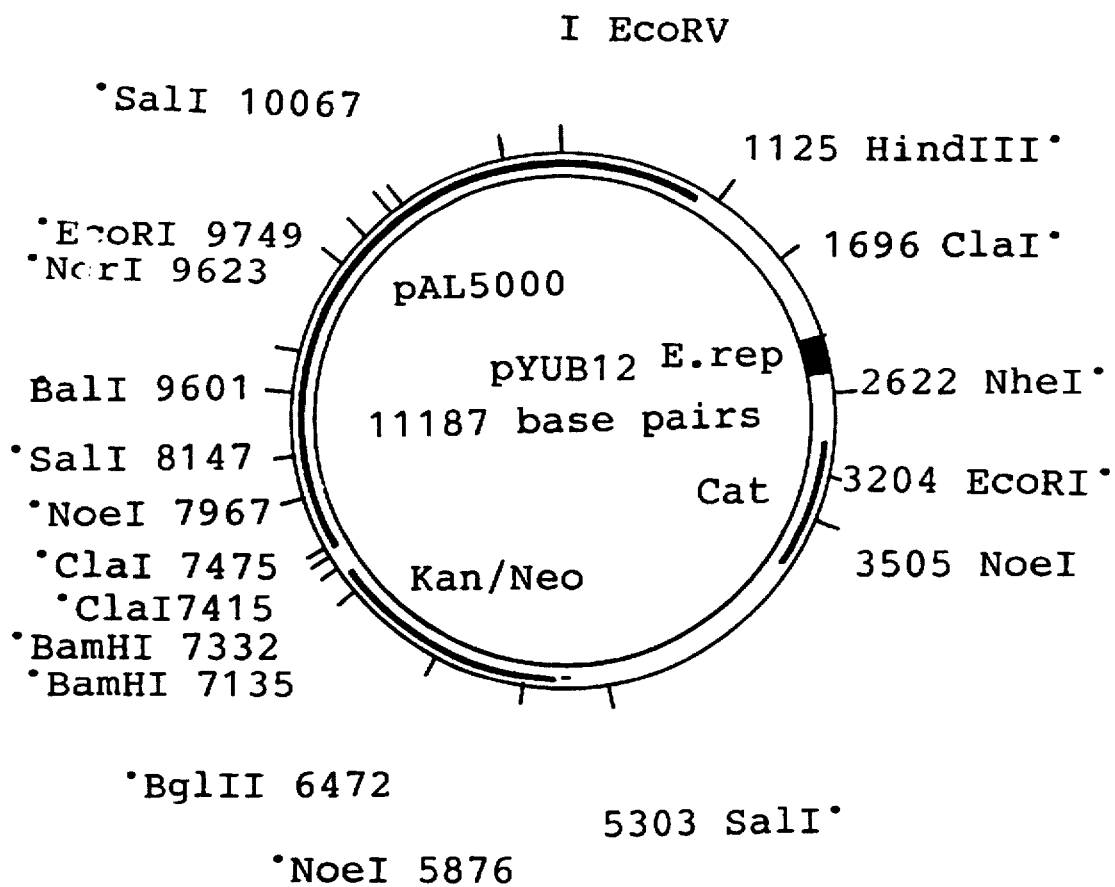
FIG. 3 illustrates the plasmid pYUB12 described in Example 1.
Figure 4:
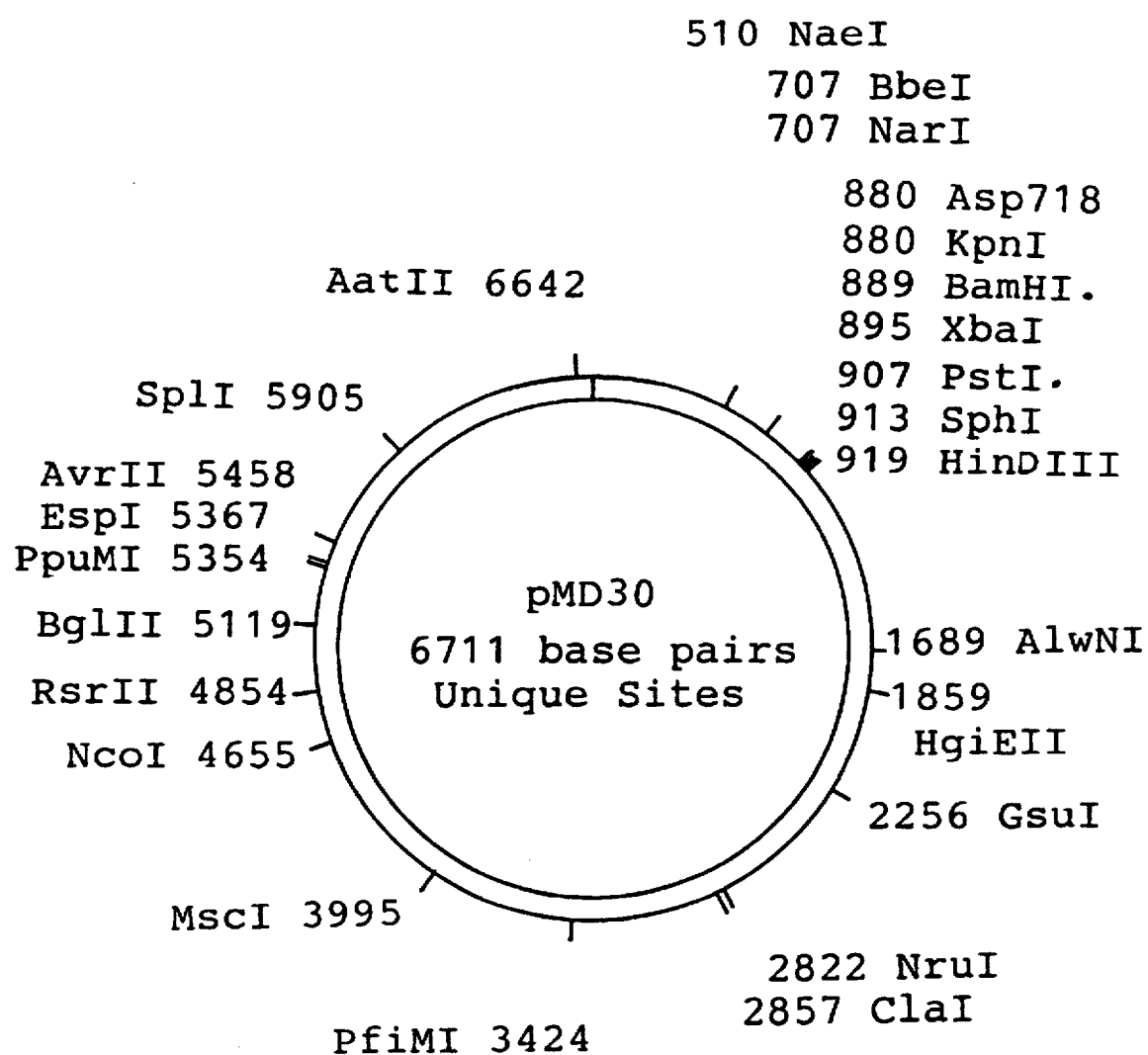
FIG. 4 illustrates the plasmid pMD30 described in Example 1.
Figure 7:
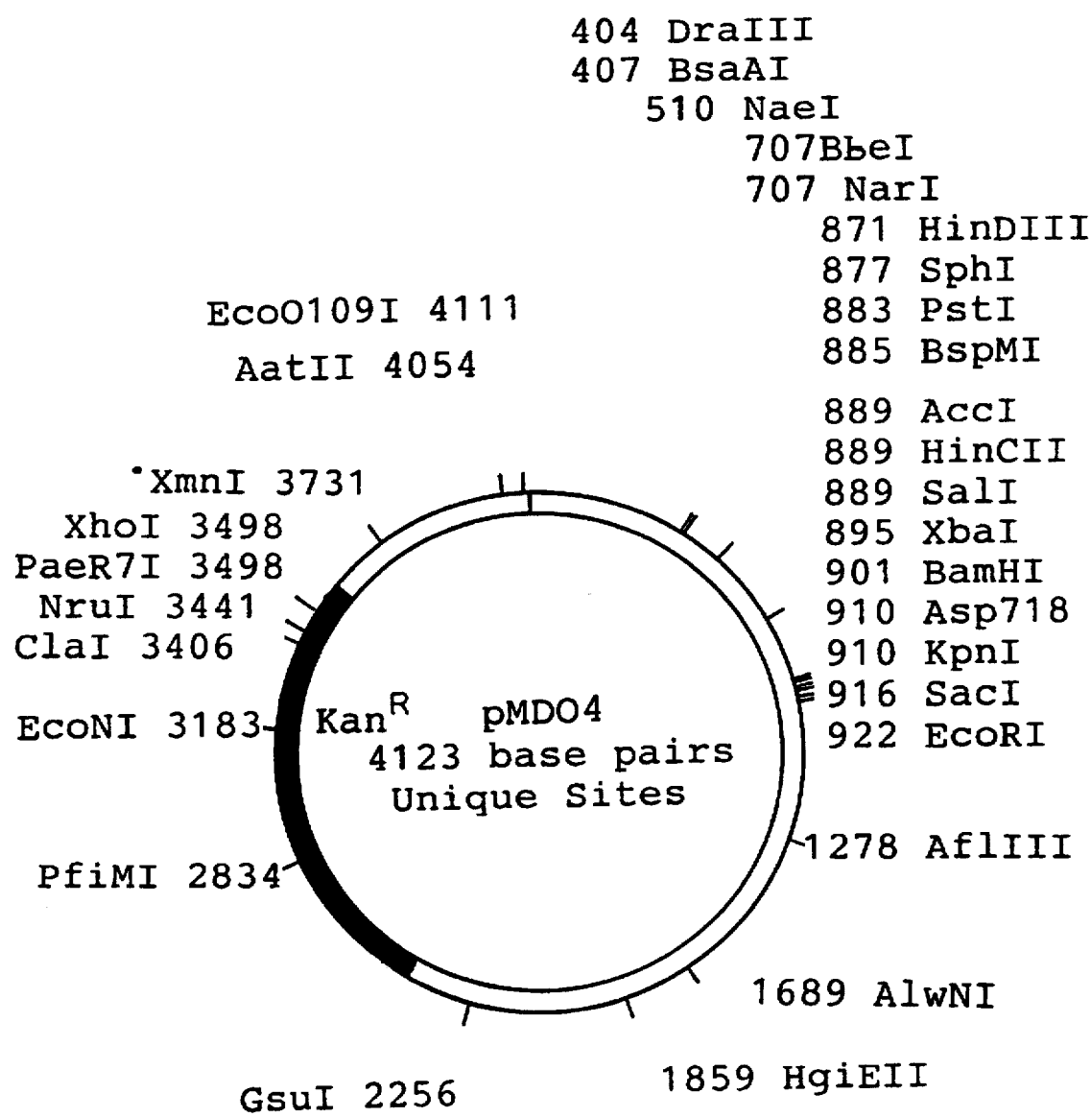
FIG. 7 illustrates the plasmid pMD04 described in Example 3.
Figure 8:
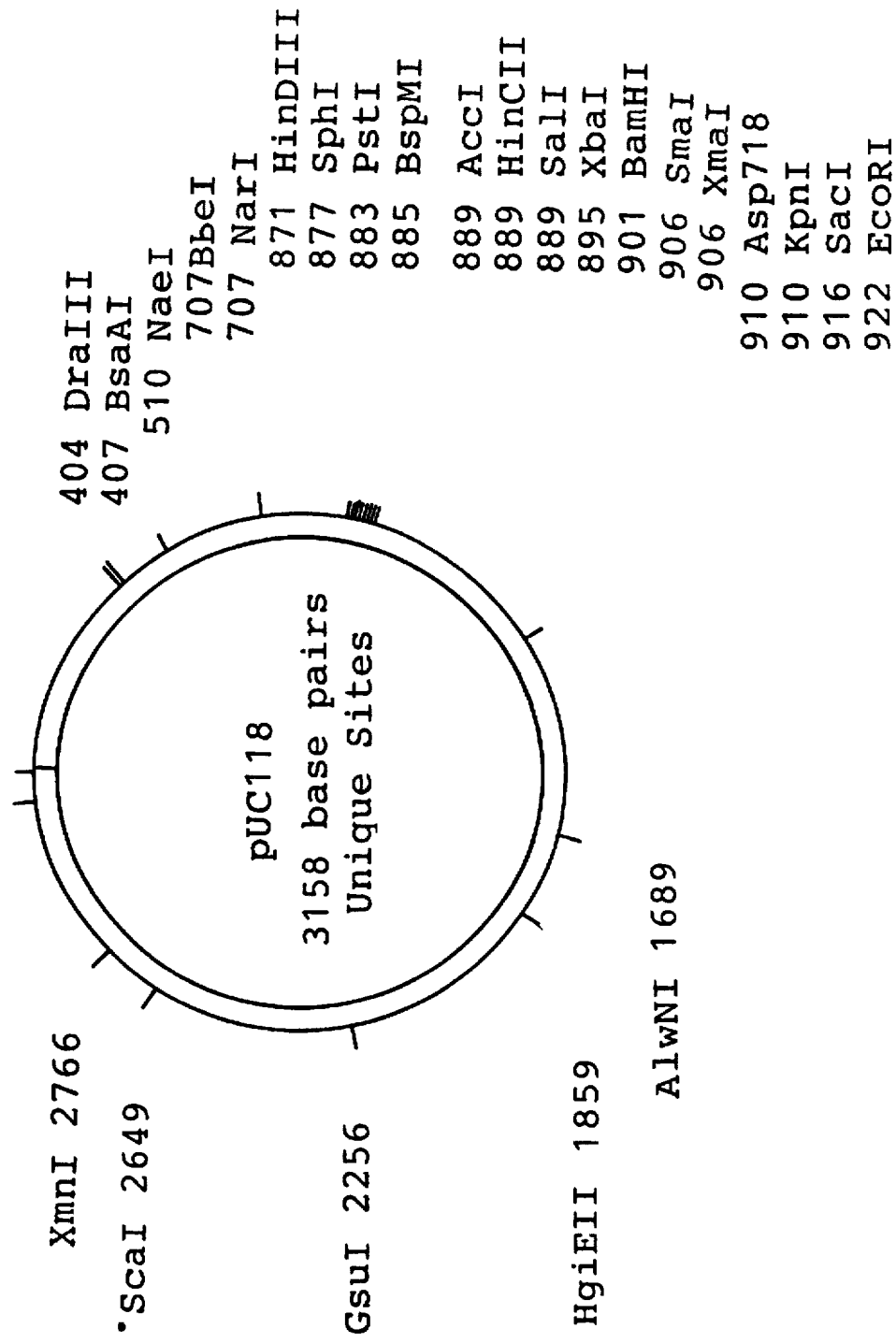
FIG. 8 illustrates the plasmid pVC118 described in Example 3.
Figure 9:
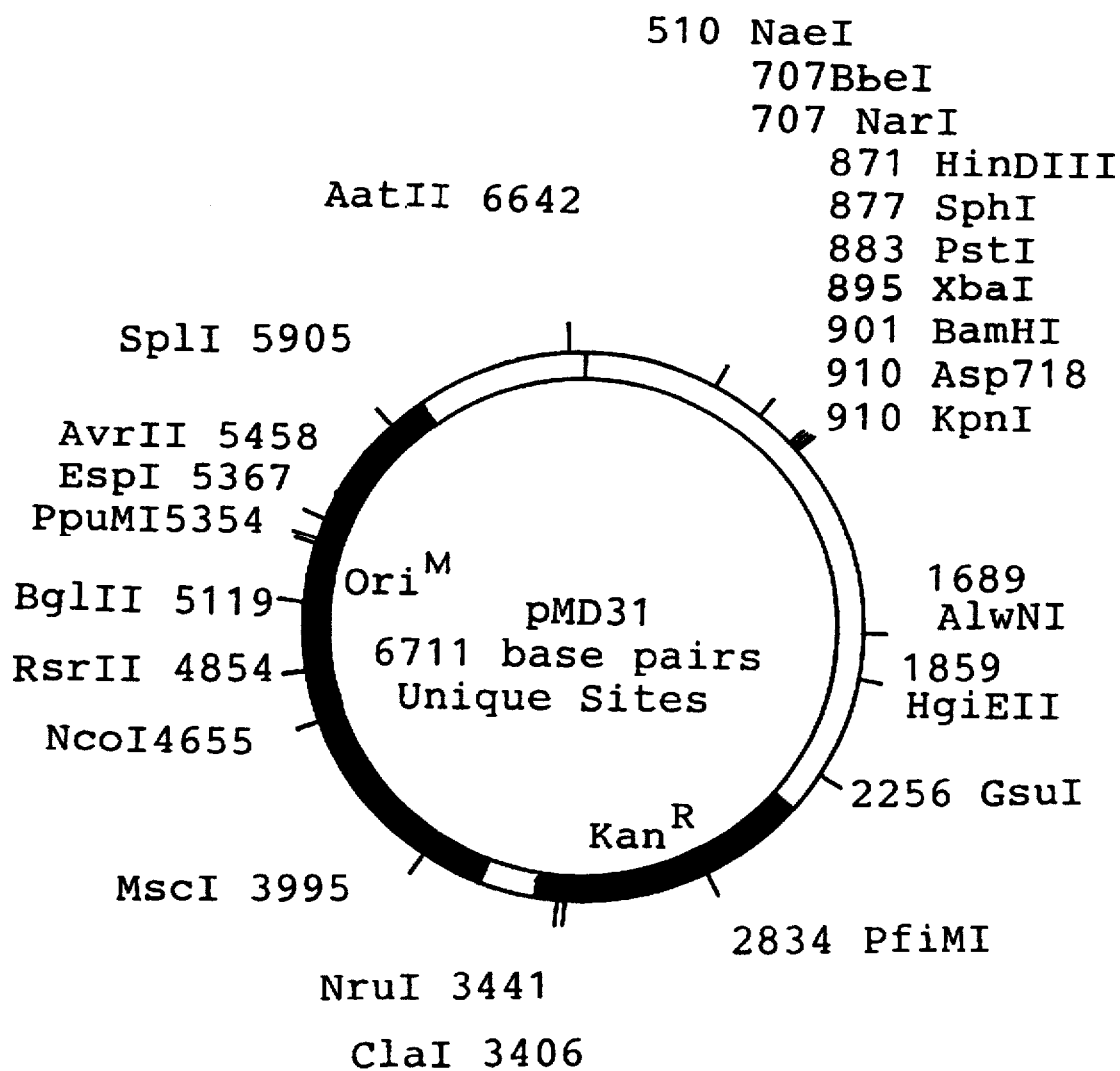
FIG. 9 illustrates the plasmid pMD31 described in Example 3.
Figure 10:
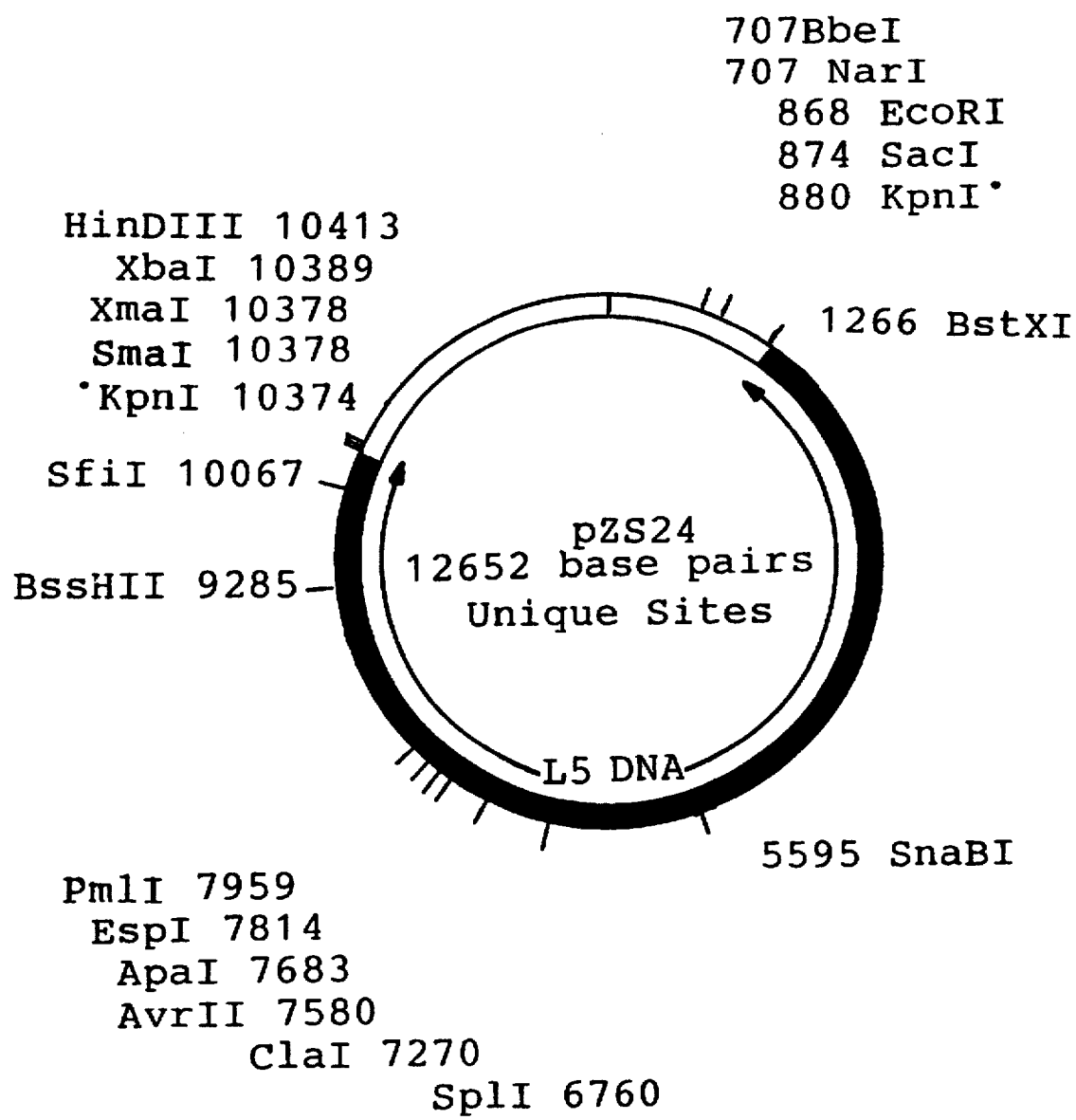
FIG. 10 illustrates the plasmid pZS24 described in Example 3.
Figure 11:
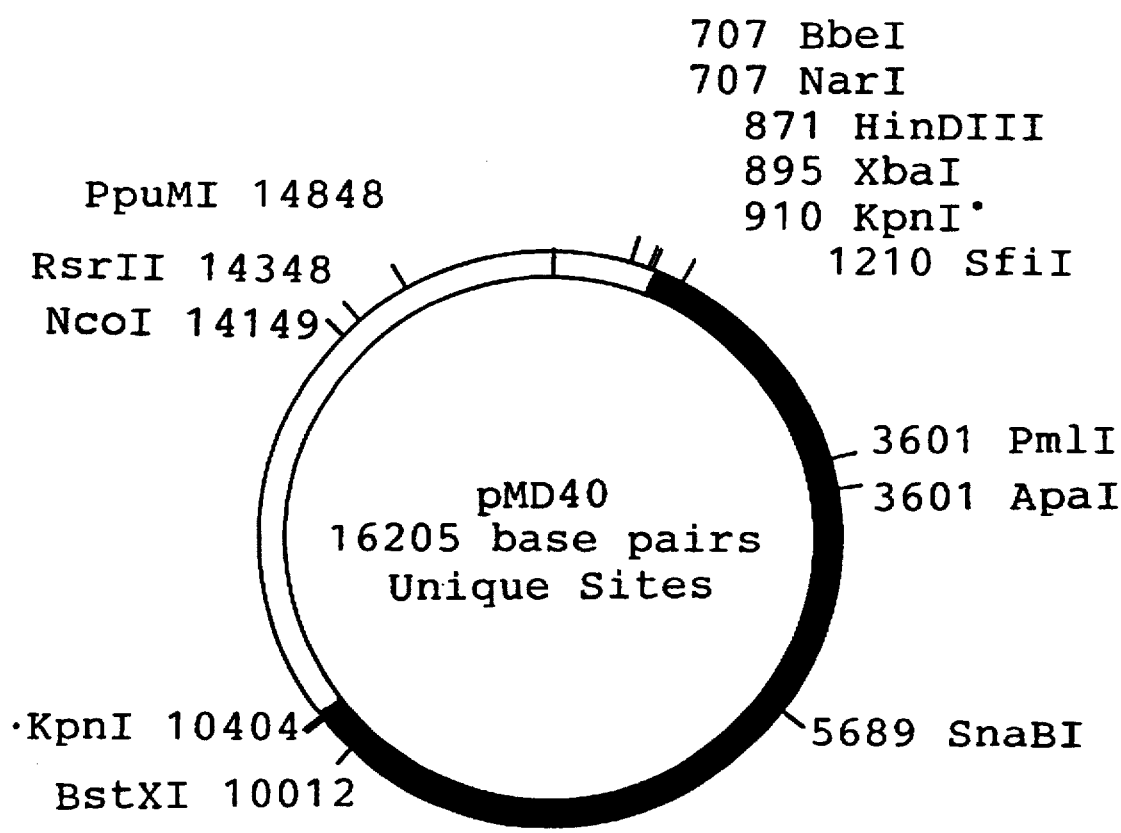
FIG. 11 illustrates the plasmid pMD40 described in Example 3.
Figure 12:
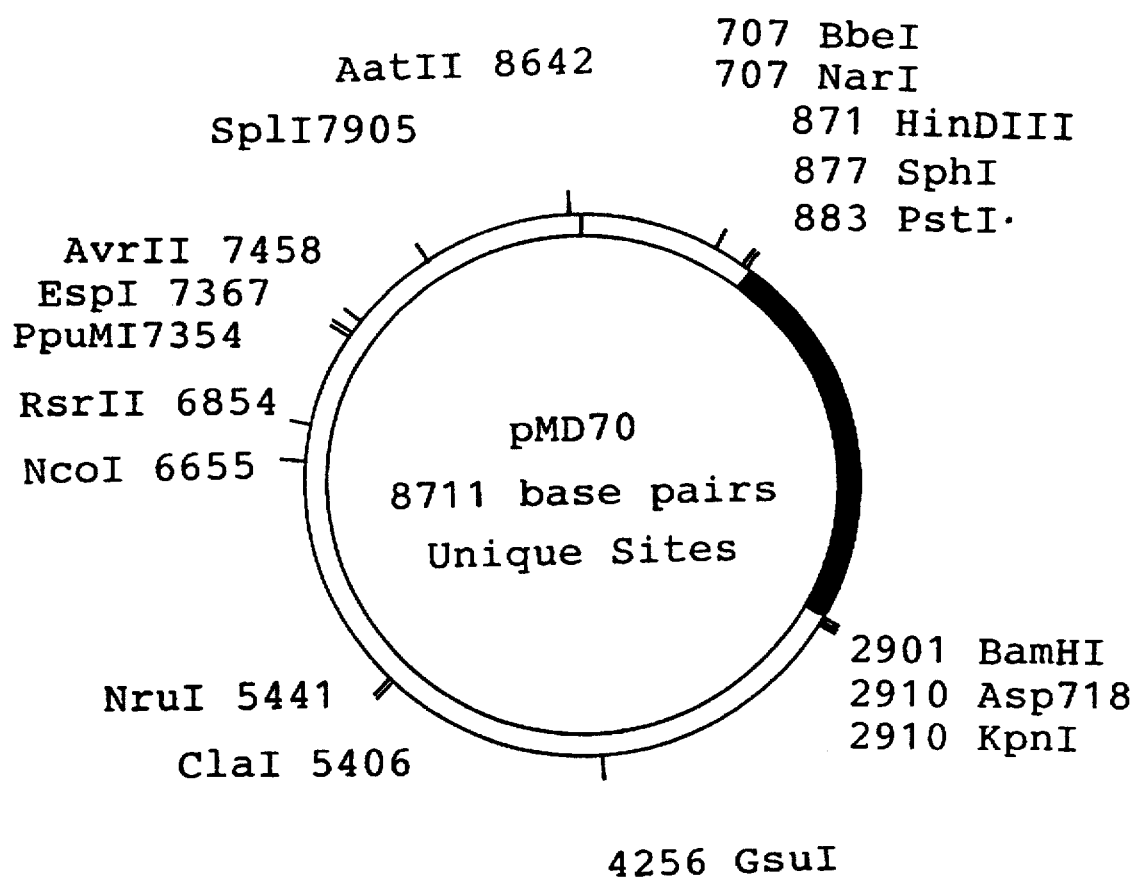
FIG. 12 illustrates the plasmid pMD70 described in Example 3.
Figure 13:
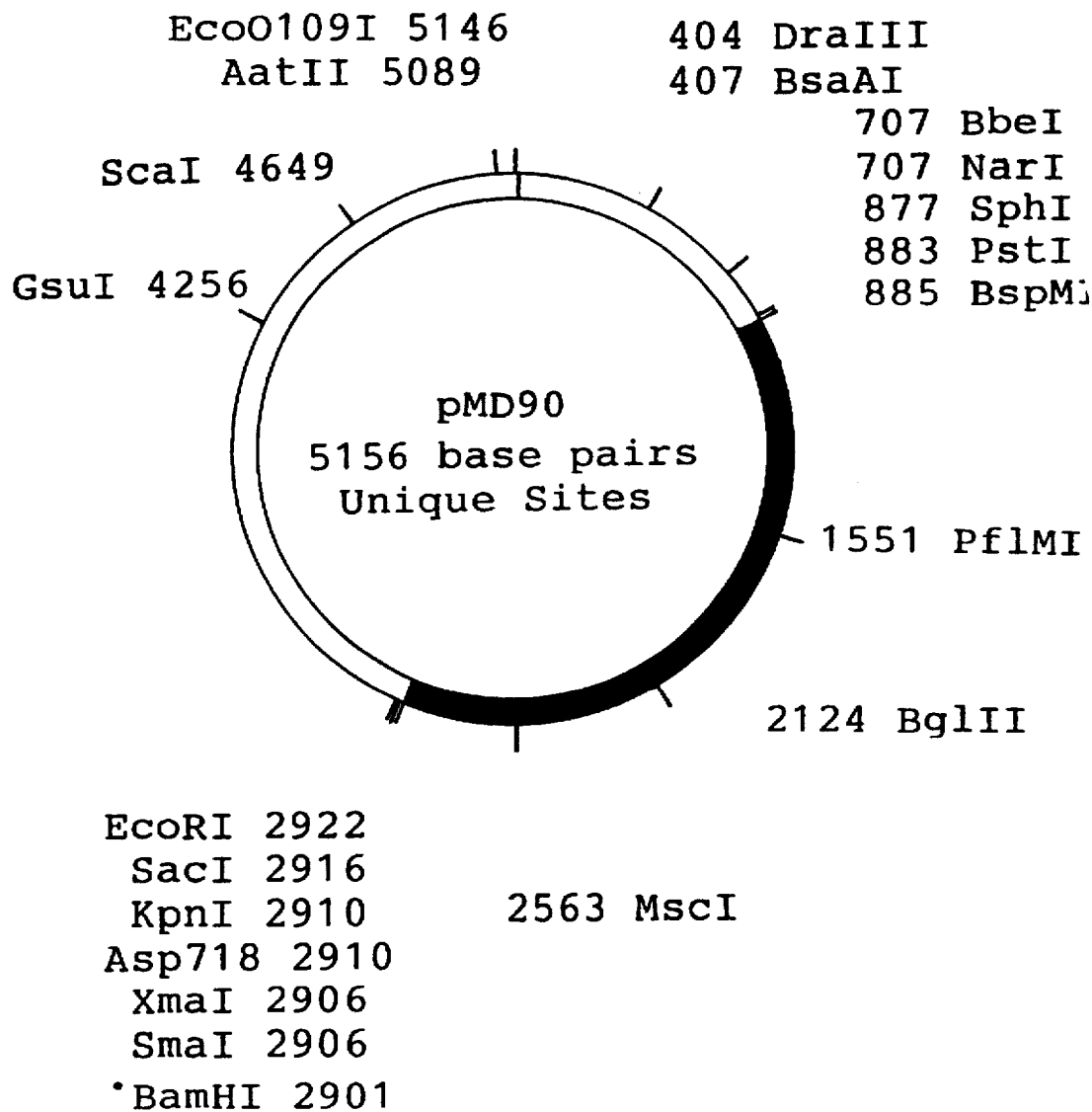
FIG. 13 illustrates the plasmid pMD90 described in Example 3.
Figure 14:
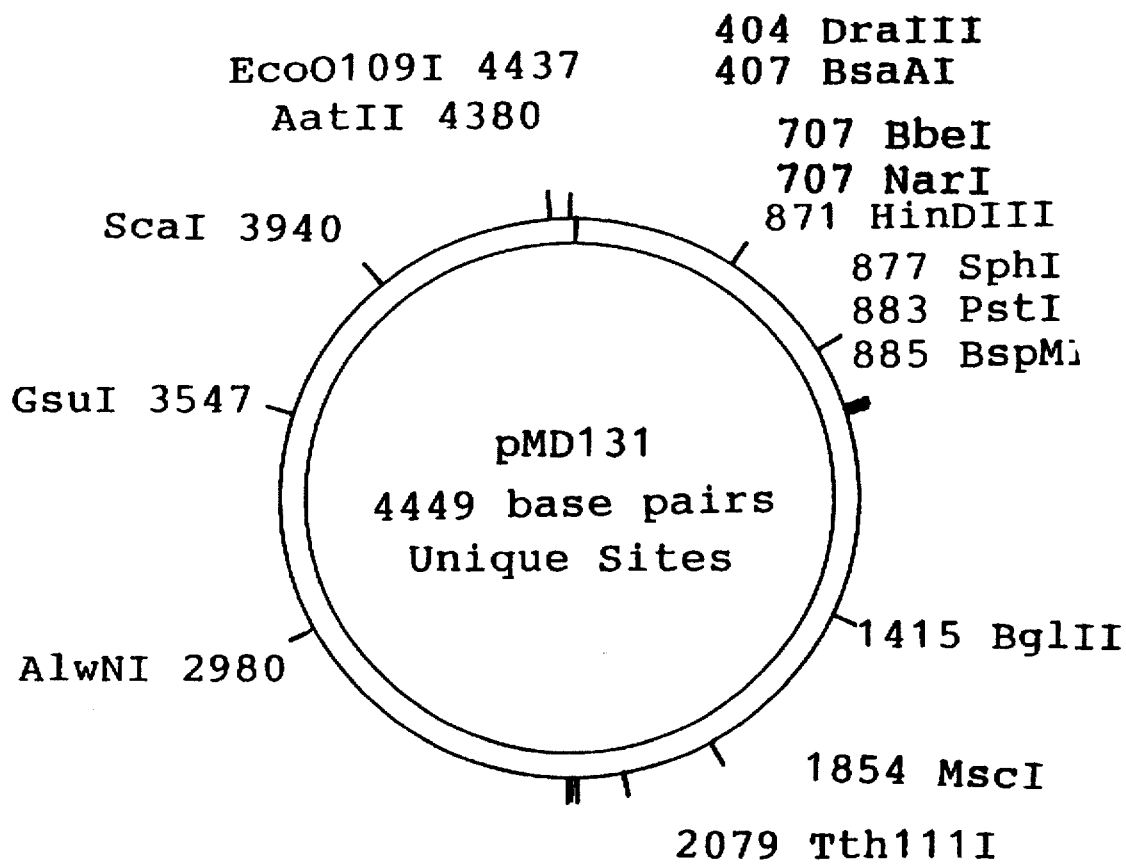
FIG. 14 illustrates the plasmid pMD131 described in Example 3.
Figure 15:
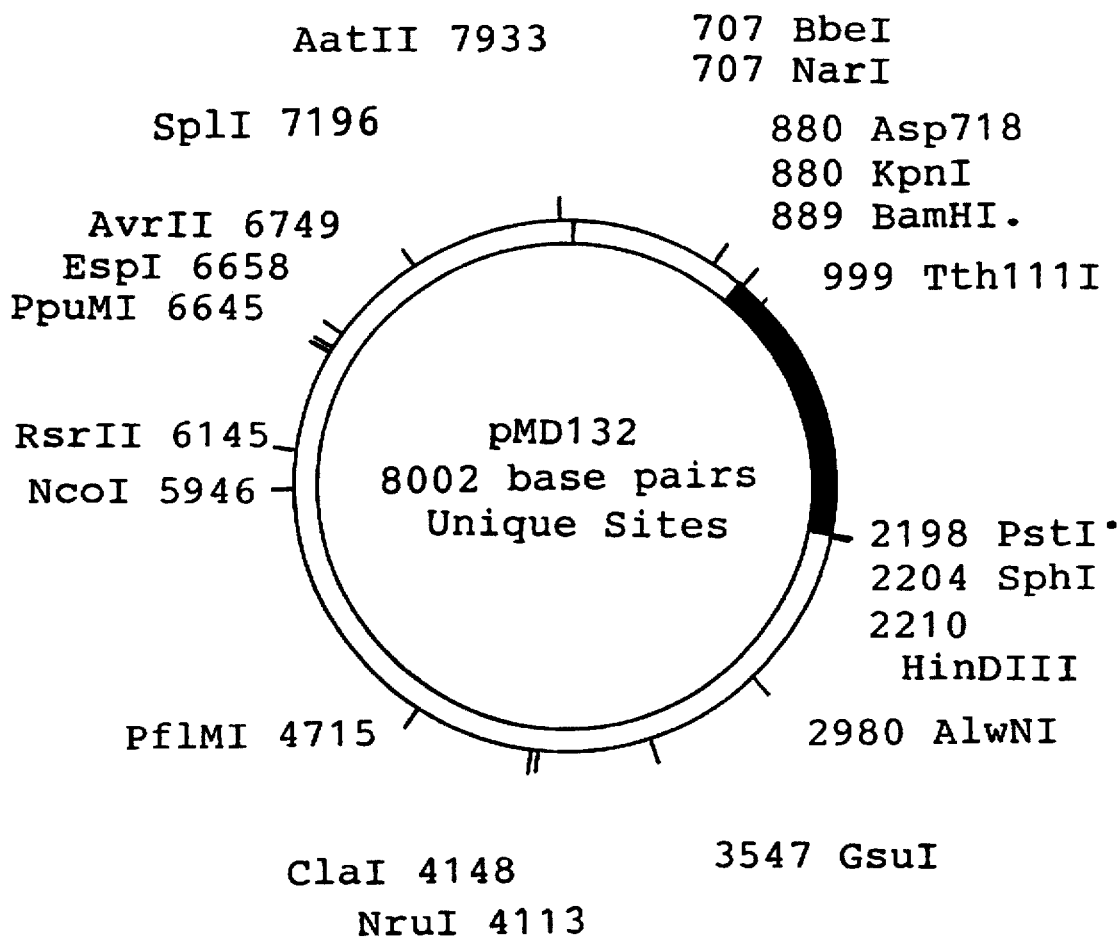
FIG. 15 illustrates the plasmid pMD132 described in Example 3.

Recombinant plasmids were constructed in which the 1.3 kb fragment of the L5 genome which contains gene 71 is inserted into an *E. coli*-mycomycobacterial shuttle vector. The construction of plasmids containing smaller segments of the 9.5 kb KpnI fragment until a plasmid was constructed which included the 1.3 kb fragment of the L5 genome containing gene 71 was as follows:

pMD04 (FIG. 7) was made by inserting the HindIII fragment (with blunt ends generated by Klenow) from pKD43 containing the kanamycin resistance gene and inserting such fragment into the ScaI site of pUC118. (FIG. 8).

pMD31 (FIG. 9) was then constructed by isolating the HpaI-EcoRV fragment from pYUB12 (FIG. 3 provided by Dr. William Jacobs), and inserting it into the XmnI site of pMD04. pMD31 is a shuttle vector which may replicate in both *E. coli* and *M. smegmatis*, and contains a kanamycin resistance gene for selection in both bacterial species.

pZS24 (FIG. 10) contains the 9.5 kb KpnI fragment of phage L5 inserted into the KpnI site of pUC119 (FIG. 1). pZS24 was constructed by gel purification of the 9.5 kb fragment and ligating into the KpnI site of pUC119. The 9.5 kb KpnI fragment of pZS24 was then isolated; and inserted into the KpnI site of pMD31 to make pMD40 (FIG. 11). The SnaBI-PstI 2 kb fragment of pMD40 was then isolated with blunt ends and inserted into the blunted XbaI site of pMD31 to form pMD70 (FIG. 12). The BamHI-PstI 2 kb fragment is isolated from pMD70 and inserted into pUC118 cut with BamHI and PstI to form pMD90 (FIG. 13). pMD90 is digested with SalI, which cuts twice, and then religated to form pMD131. (FIG. 14). A 1.3 kb BamHI-PstI fragment is removed from pMD131, and inserted into the BamHI-PstI site of pMD30 to make pMD132 (FIG. 15). These plasmids also carry the aph gene from Tn903 (provided by K. Derbyshire and Nigel Grindley of Yale University) that confers resistance to kanamycin, and an *E. coli* origin of replication.

B. Phage Selection of Gene 71 Transformants

Plasmid DNA's from pYUB12 or pMD70 were then electroporated into *M. smegmatis*, according to the procedure of Snapper et al. (1988), and transformants were selected either by kanamycin selection (Snapper et al., 1988), or as survivors of a phage infection. Phage infection with L5c(d1) with a multiplicity of infection (m.o.i.) of about 10 according to the procedure of Snapper et al. (1988) (i.e., 10 phage particles to each bacterial cell.) after a period of recovery from electroporation, efficiently killed non-transformed cells, but not plasmid-transformed cells. The phage-selected transformants also were determined to be resistant to kanamycin, thus indicating that they are true transformants.

*M. smegmatis* strain mc² 155 cells (approximately $4 \times 10^8$ cells prior to electroporation) were electroporated with pYUB12, pMD70, or without DNA, and incubated for 1 hour in broth to allow expression of the selectable genes. Transformants were selected either with kanamycin (Snapper et al., 1988) or by phage D29 infection.

The procedure for D29 phage infection was as follows:

D29 phages were added to *M. smegmatis* cells such that the multiplicity of infection was about 10. This is typically about $4 \times 10^9$ plaque forming units (pfu) of phage. The phages were allowed to adsorb to the bacteria by incubation at 37° C. for 30 minutes. The entire sample was then plated onto solid media.

From several independent experiments carried out as hereinabove described, it was found that spontaneous D29 resistant mutants (from non-transformed mycobacteria or mycobacteria transformed with pYUB12) occur at a higher frequency (about 1–10 transformants/ug DNA) than non-transformed kamamycin resistant mutants wherein almost no transformants were detected. Such spontaneous D29 resistant mutants were found, after purification, to be resistant to both D29 and L5 but sensitive to heteroimmune mycobacteriophages such as TM4, thus indicating that such colonies are true D29 resistant derivatives. Also, as expected, the majority of pMD70 D29-selected transformants are also kanamycin resistant (of 148 colonies in one experiment and 37 in another, all were kanamycin resistant).

EXAMPLE 4

Phage Selection of Integrated Gene 71 Transformants

Figure 16:
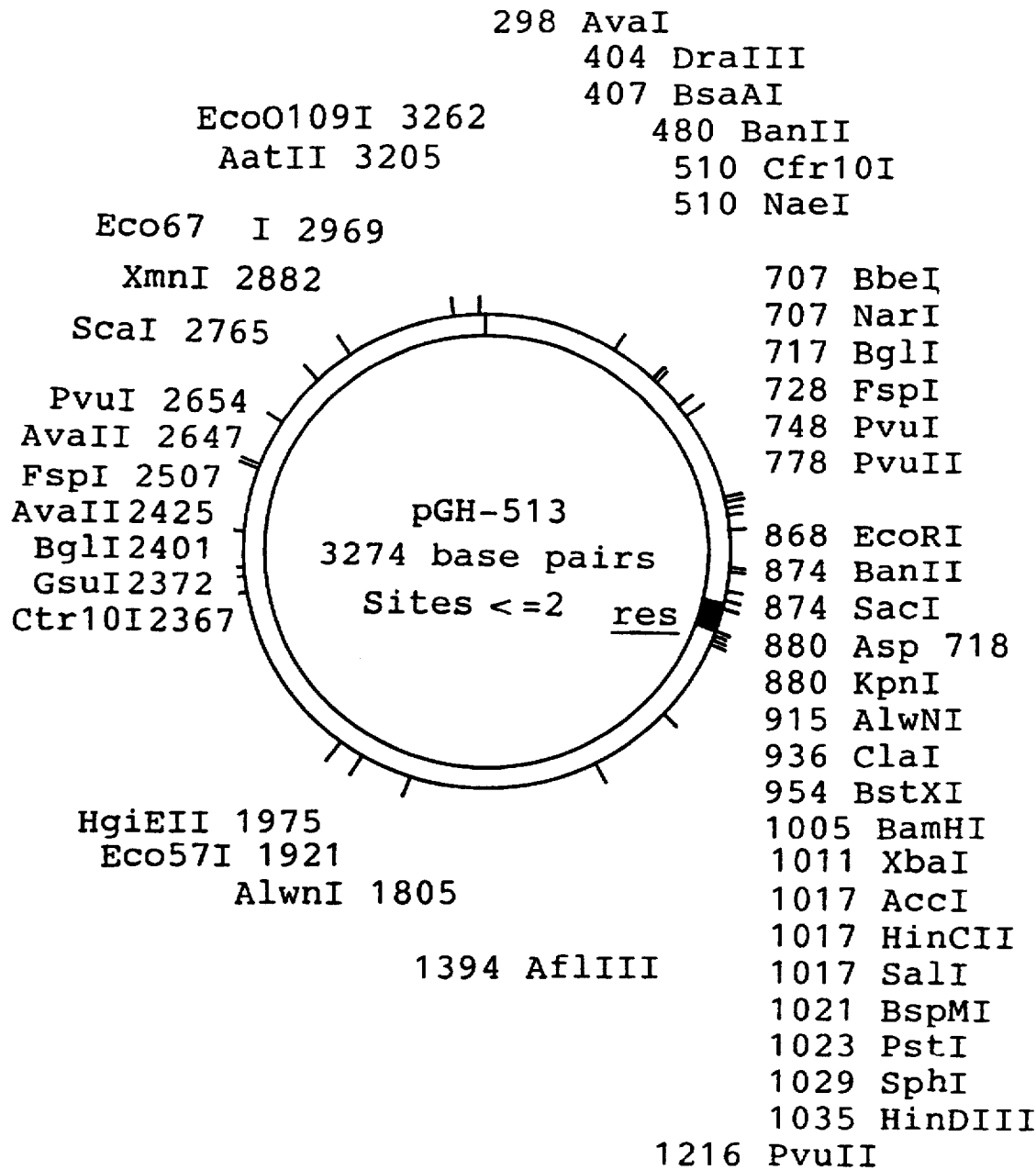
FIG. 16 illustrates the plasmid pGH513 described in Example 4.
Figure 17:
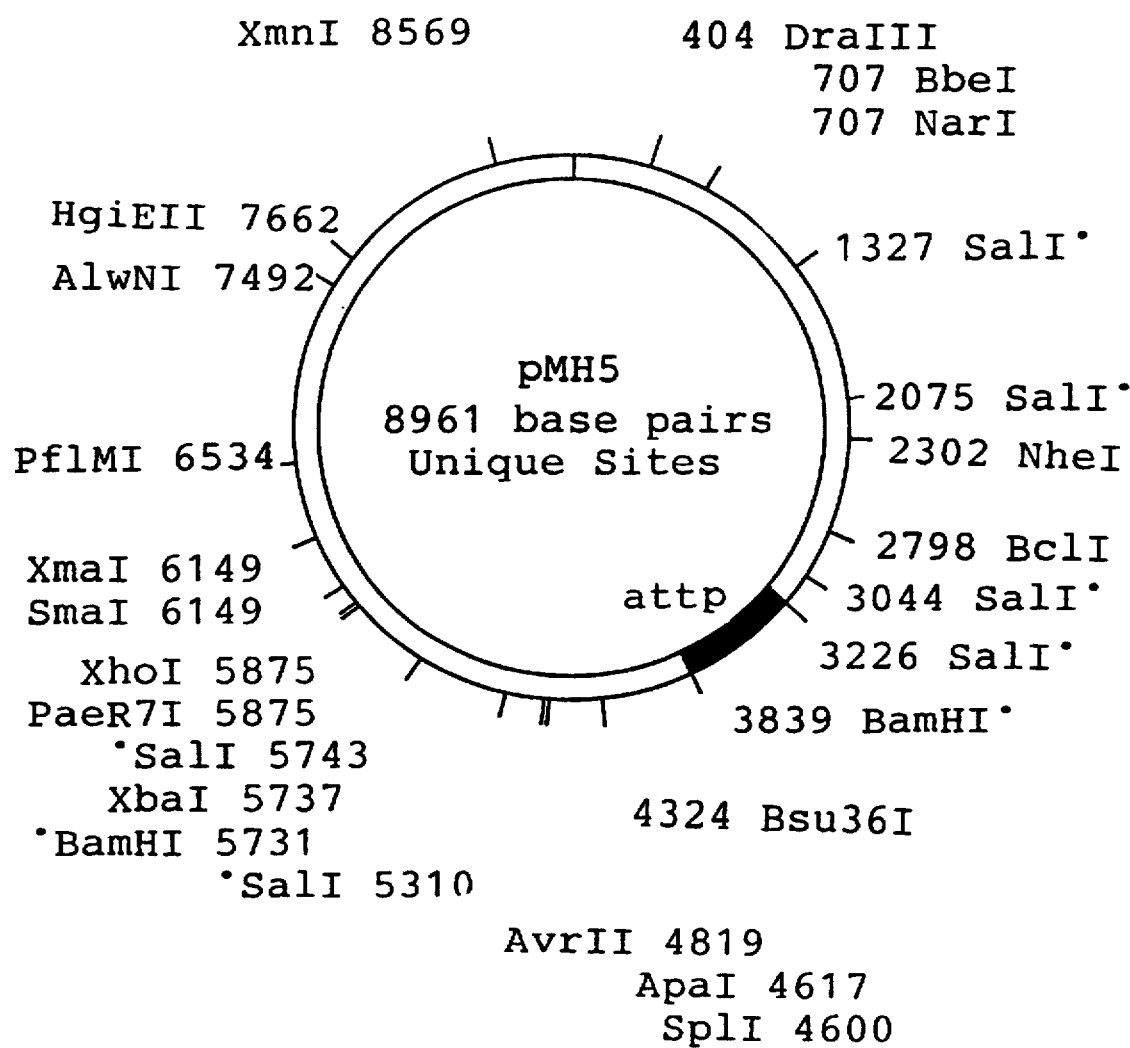
FIG. 17 illustrates the plasmid pMH5 described in Example 4.
Figure 18:
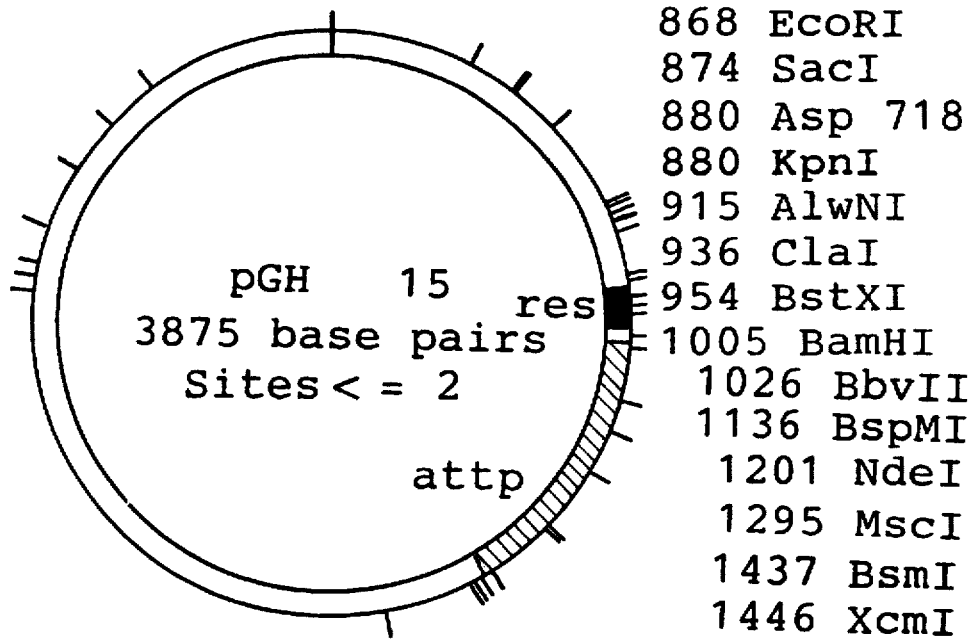
FIG. 18 illustrates the plasmid pGH515 described in Example 4.
Figure 19:
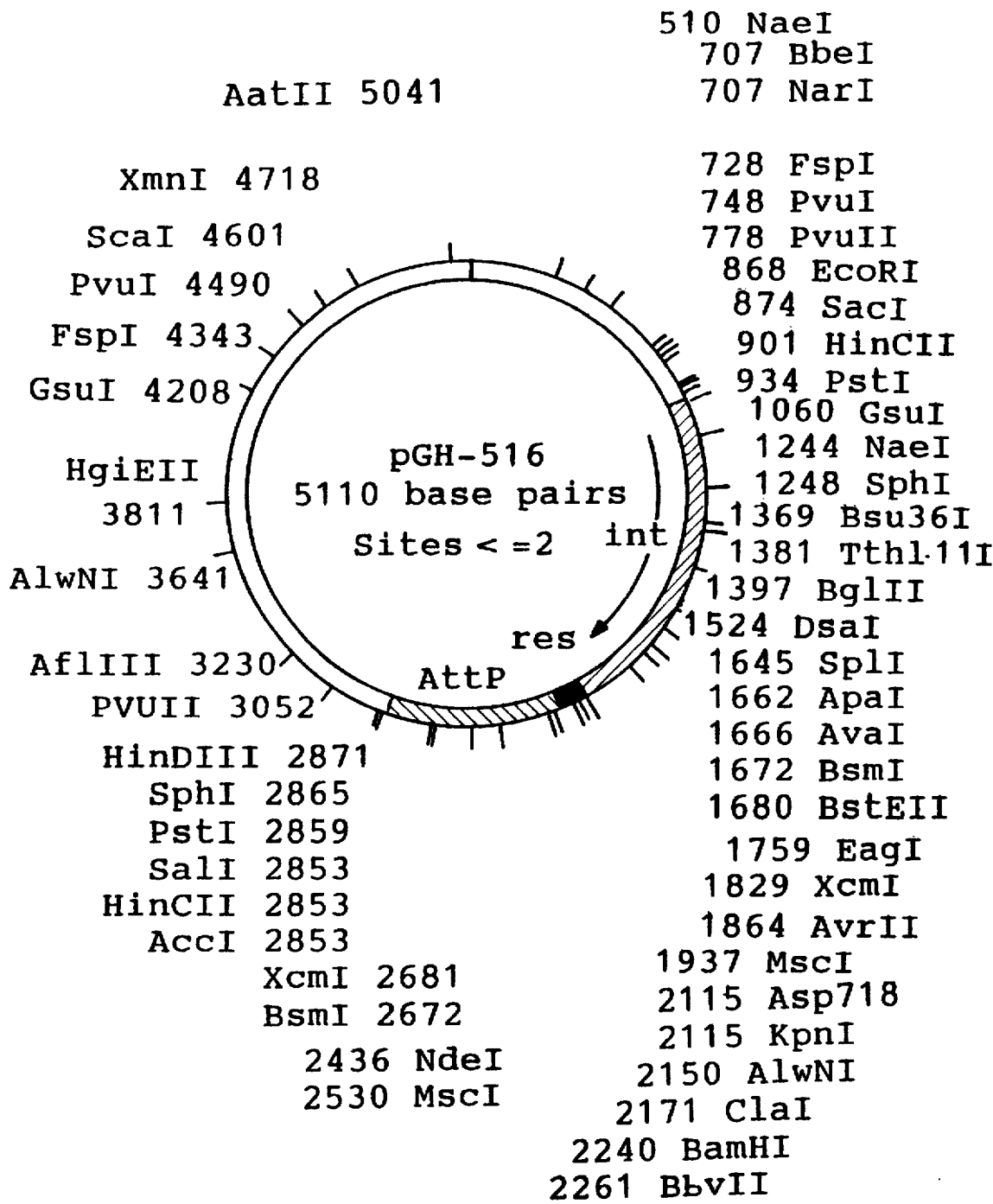
FIG. 19 illustrates the plasmid pGH516 described in Example 4.
Figure 20:
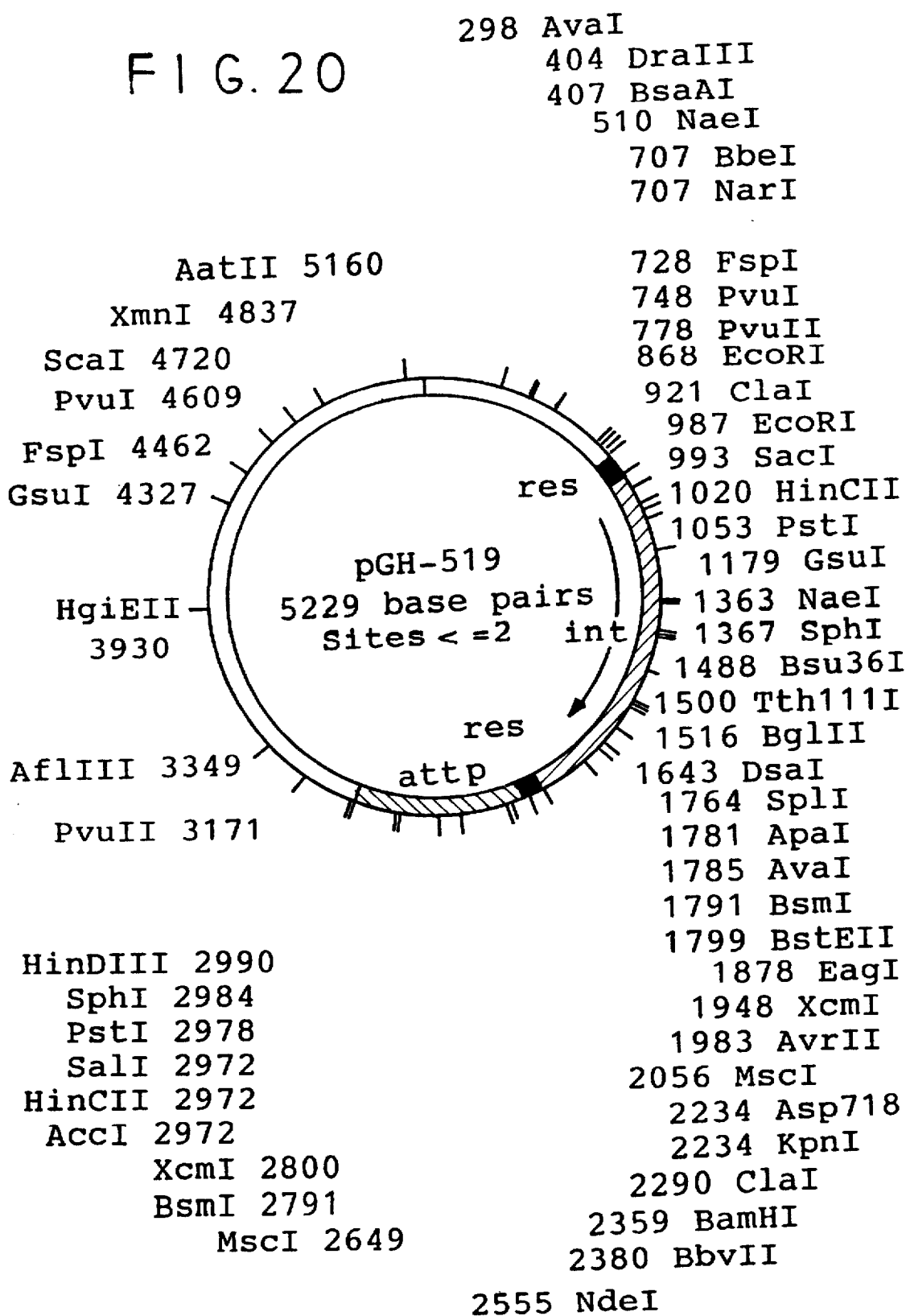
FIG. 20 illustrates the plasmid pGH519 described in Example 4.
Figure 21:
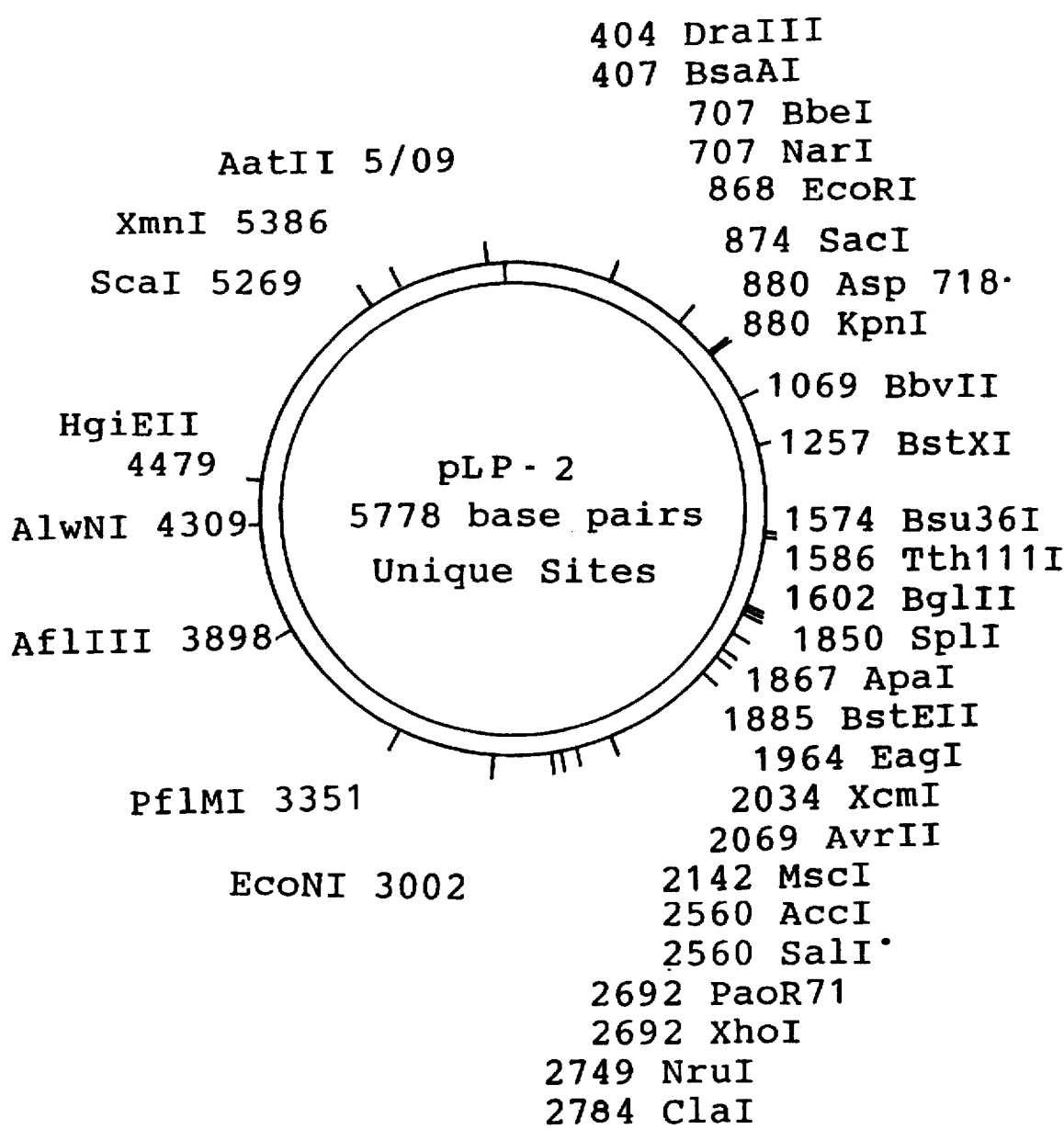
FIG. 21 illustrates the plasmid pLP2 described in Example 4.
Figure 22:
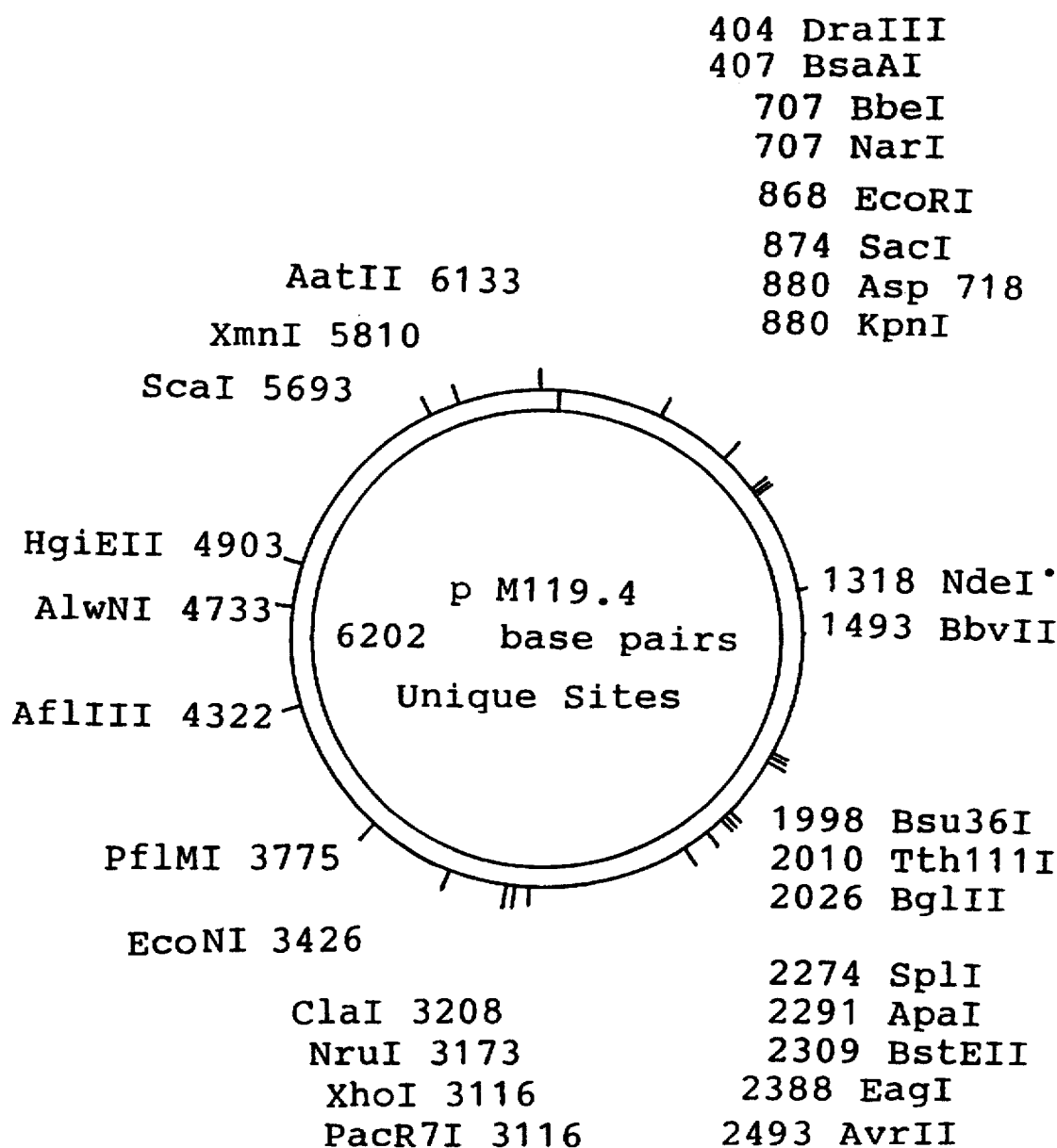
FIG. 22 illustrates the plasmid pMH9.4 described in Example 4.
Figure 23:
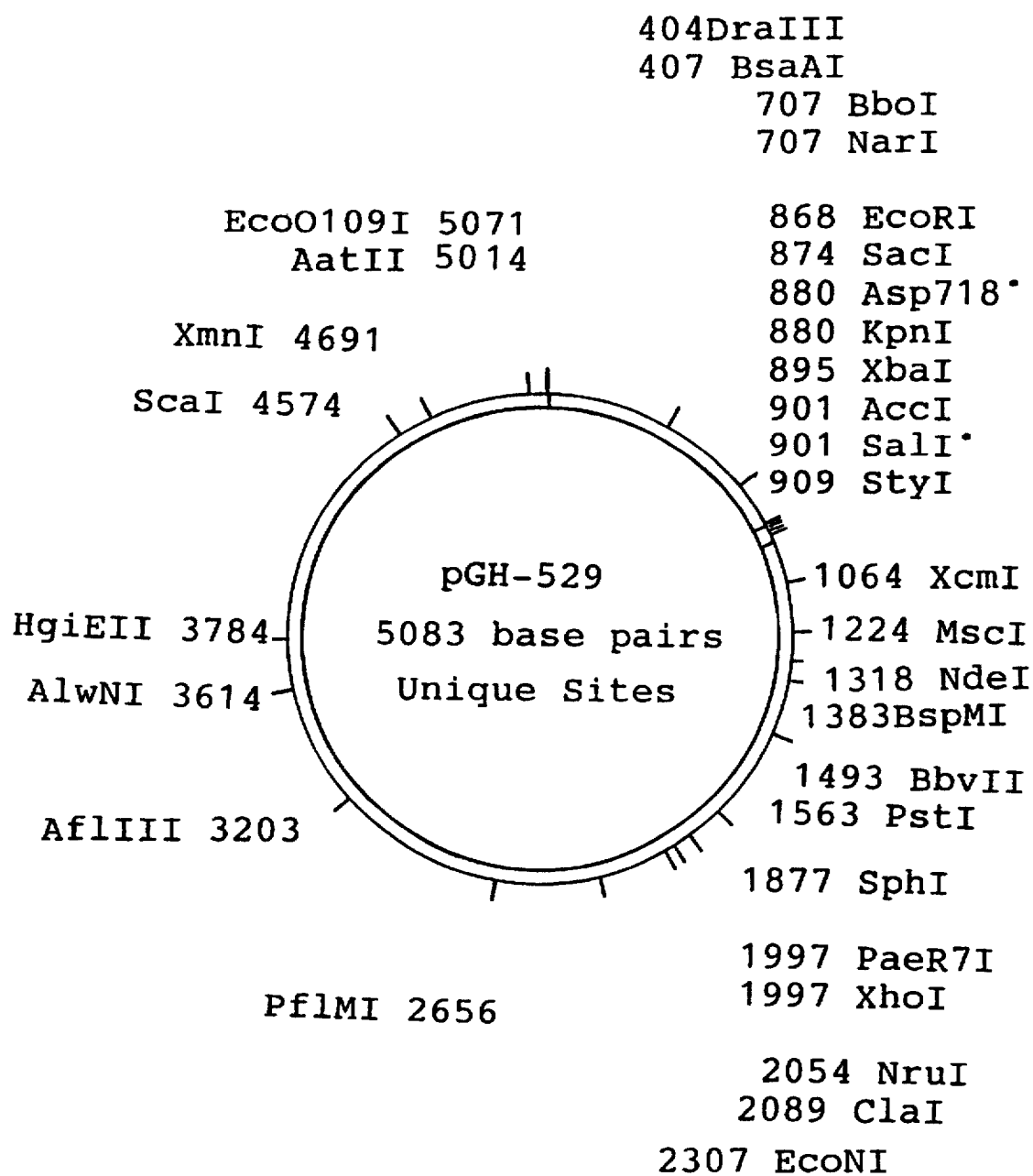
FIG. 23 illustrates the plasmid pGH529 described in Example 4.
Figure 24:
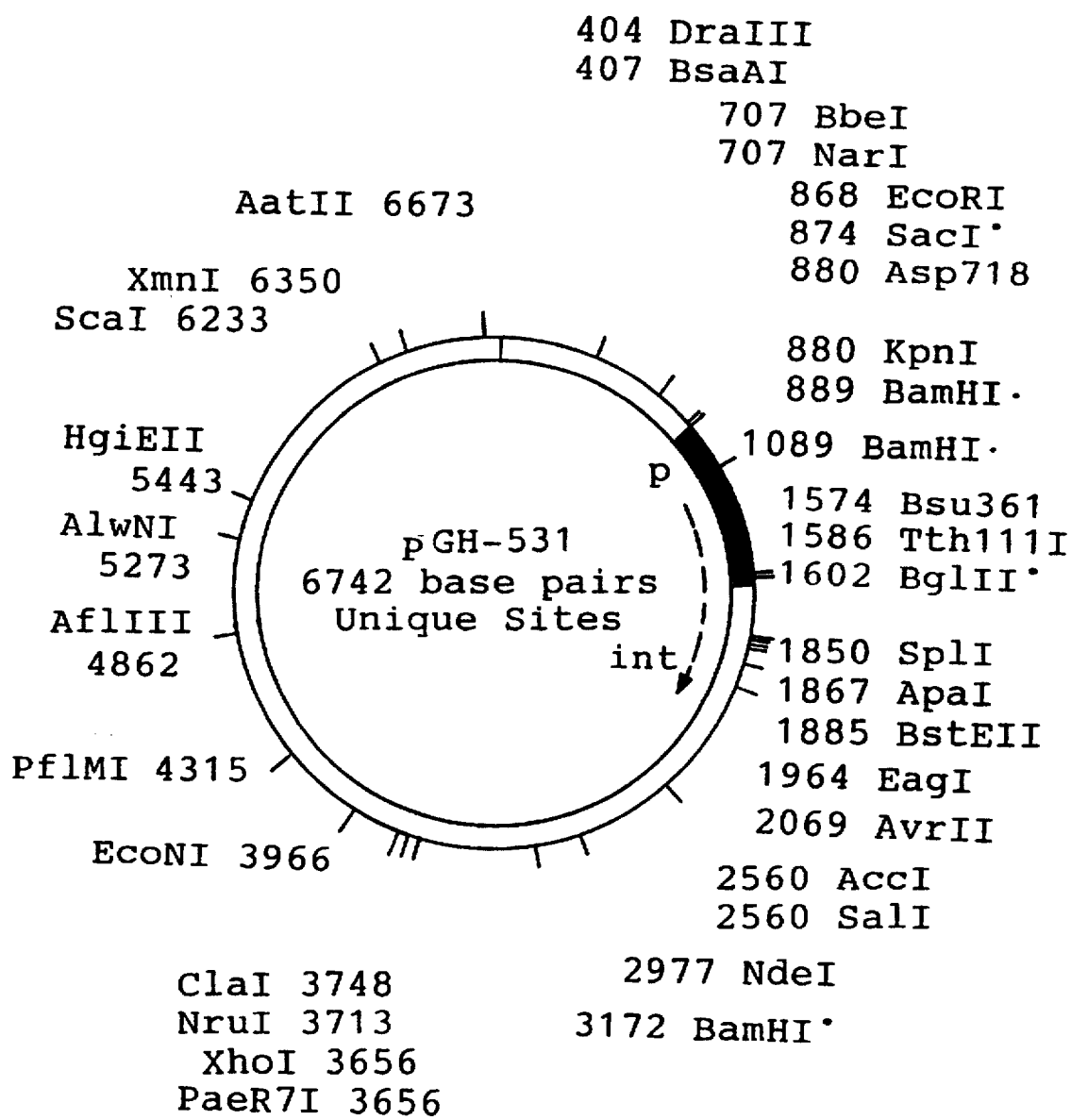
FIG. 24 illustrates the plasmid pGH531 described in Example 4.
Figure 25:
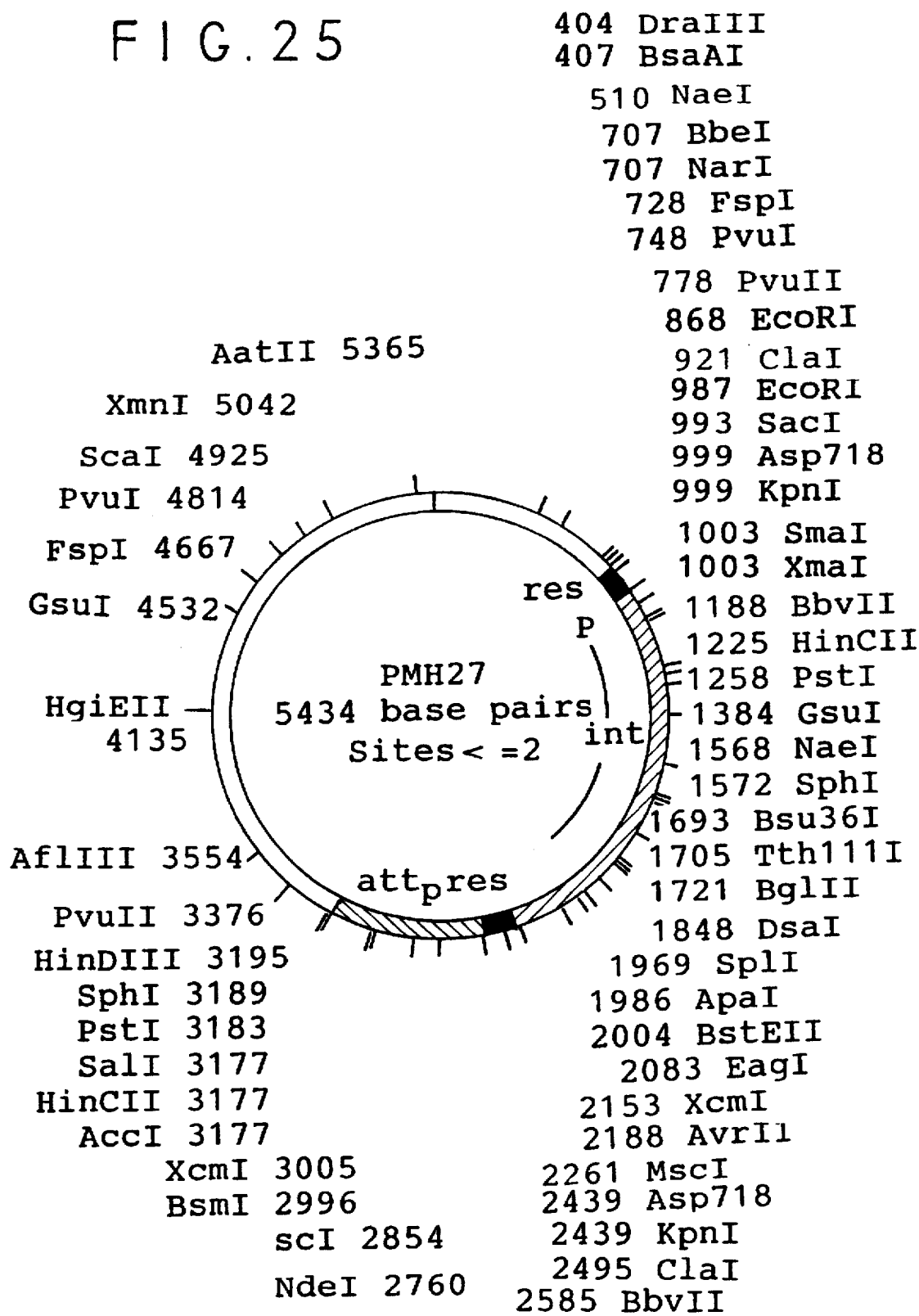
FIG. 25 illustrates the plasmid pMH27 described in Example 4.
Figure 26:
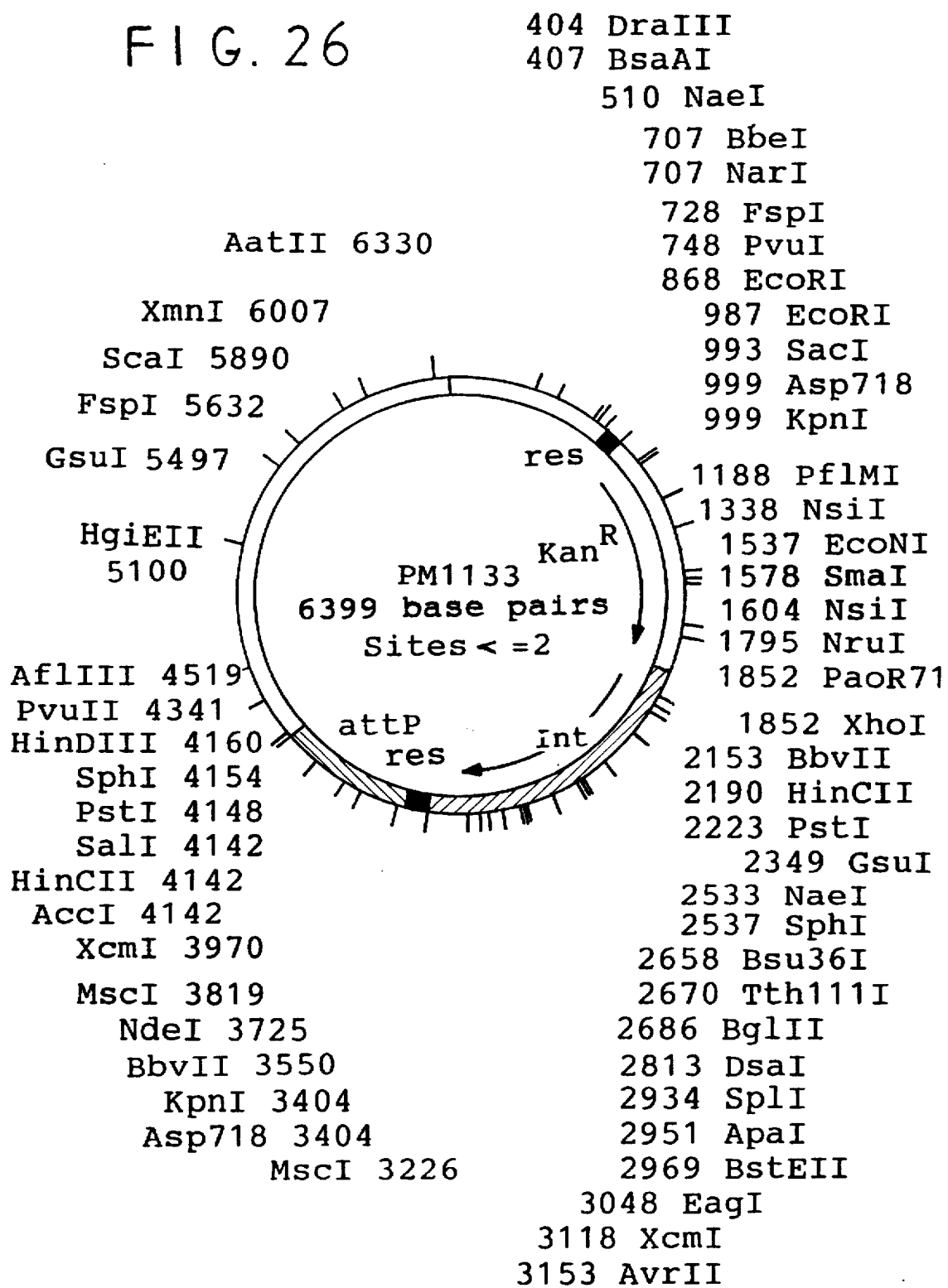
FIG. 26 illustrates the plasmid pMH33 described in Example 4.
Figure 27:
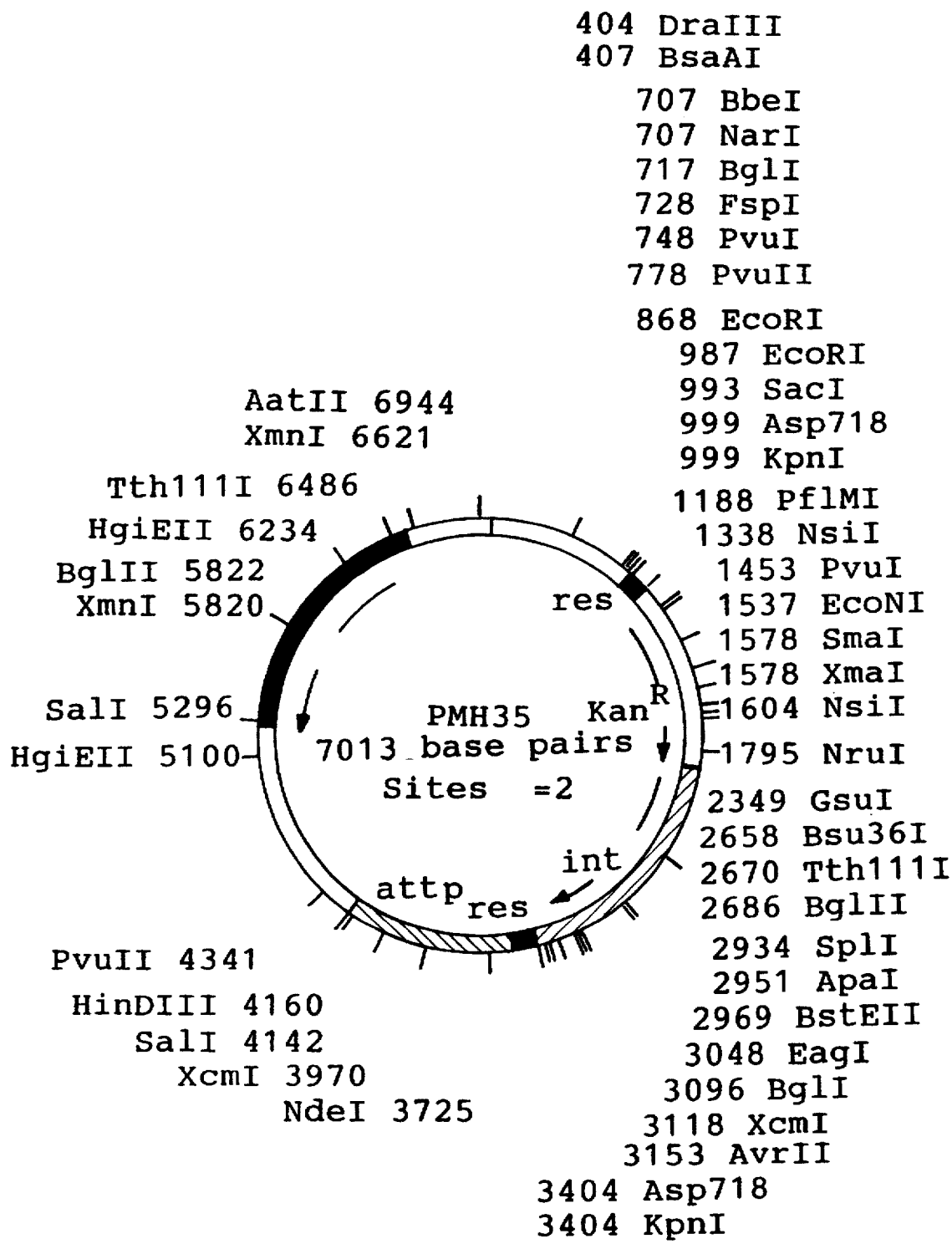
FIG. 27 illustrates the plasmid pMH35 described in Example 4.

In this example, the integrating vector containing gene 71 is pMH35, the construction of which is detailed as follows:

pNG199 (obtained from Dr. Nigel Grindley) is a plasmid that contains multiple copies of a res site of transposon inserted into a pUC vector. When two res sites are directly oriented, such sites encode an active site for resolvase which resolves plasmids into singly-linked catenanes. A PvuII (130 bp) fragment of pNG199, containing the res site, was purified and inserted into the vector pUC118 (FIG. 8) at the SmaI site. The resulting plasmid is pGH513 (FIG. 16).

pMH5 (FIG. 17), which contains the mycobacteriophage L5 attP site was digested with BamHI and SalI, and the 613 bp fragment containing the L5 attP site was inserted between the BamHI and SalI sites of pGH513 to form pGH515 (FIG. 18). pGH515 thus contains a single res site and an attP site.

pGH515 was digested with BamHI and PvuII (FIG. 18), and a 1.2 kb fragment containing the int gene of mycobacteriophage L5 was inserted into the Asp718 site of pGH515 to form pGH516. (FIG. 19). pGH516 contains the attP site and int gene of L5, which are separated by a single res site.

pGH318 (obtained from Dr. Nigel Grindley), like pNG199 is a plasmid that contains multiple copies of a res site of transposon δ inserted into a pUC vector. pGH318 was digested with EcoRI, and a 130 bp fragment containing the res site was inserted into the EcoRI site of pGH516 to form pGH519. (FIG. 20). pGH519 contains the attP site and int gene of L5 plus two res sites which are in direct orientation. It was found that the segment of DNA in pGH519 that contains the int gene is not expressed in mycobacteria. Therefore, it was necessary to replace the upstream sequences with the sequence (i.e., the promoter sequence) required for int expression. This was achieved as follows:

pLP2 (FIG. 21) was derived from pMH9.4 (FIG. 22-Lee et al., *PNAS*, 88:3111–3115, April 1991) by cutting with NdeI and XbaI, blunt ending the ends with Klenow, and religation. pLP2 thus has a defective attP site, but has a functional int gene.

pGH529 (FIG. 23) was derived by digesting pMH9.4 (FIG. 22) by cutting with SphI, and religating. pGH529 has a functional attP site, but the int gene is non-functional. pGH531 (FIG. 24) was then constructed by ligating the 1680 bp Asp718-SalI fragment from pLP2 (FIG. 21) to the 5062 bp Asp718-SalI fragment from pGH529 (FIG. 23). pGH531 was then digested with BglII and SacI, and a 728 bp BglII-SacI fragment from pGH531 was inserted into the BglII-SacI piece of pGH519 to form pMH27 (FIG. 25).

pMH27 was then opened at the SmaI site and an aph kanamycin resistance cassette from pKD43 was inserted. The resulting plasmid is called pMH33 (FIG. 26).

pMH33 was then cut with DraI, and a HindIII-Bam HI fragment (1.3 kb) from pMD131 (FIG. 14) that contains gene 71 was inserted to form pMH35 (FIG. 27).

Thus, pMH35 includes an attP site, an integrase (int) gene, gene 71, and a gene encoding kanamycin resistance (aph gene). pMH35 is efficiently transformed through electroporation into *M. smegmatis*, and transformants can be selected by either L5c(d1) infection or by kanamycin selection.

Figure 28:
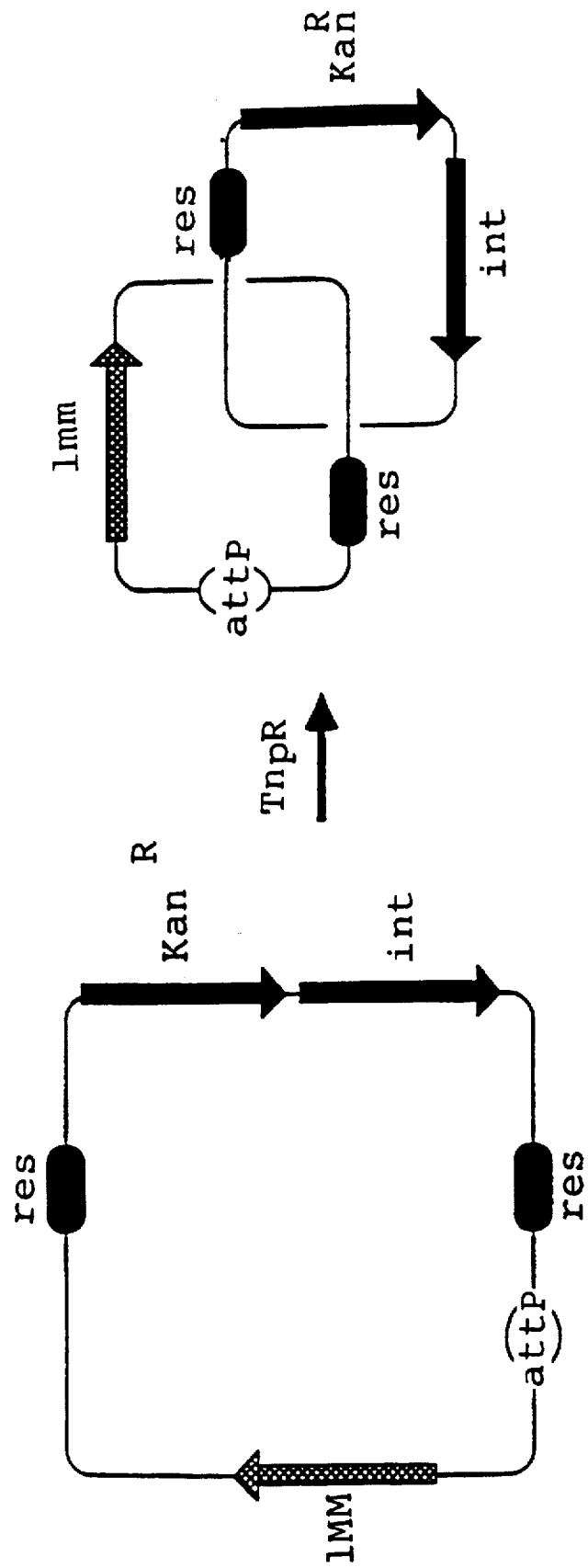
FIG. 28 shows the two singly-linked circular DNA-daughter molecules which result from reaction of plasmid pMH35 with resolvase as described in Example 4.

Because it is desirable in the final construction step of vaccine development that antibiotic resistance markers be removed, a method for removing such markers was developed. A cointegrate molecule was constructed which contains two directly oriented copies of the res site derived from transposon δ. (Hatfull et al., "Resolvases and DNA-invertases: A Family of Enzymes Active in Site-Specific Recombination," *Genetic Recombination*, Kucherlapatti and Smith, eds., ASM Press (1988)). Such directly oriented copies of the res site are contained in pMH35. An in vitro reaction using purified resolvase protein resolves the cointegrate pMH35 into two daughter molecules which are topologically linked as singly-linked circular DNA molecules (FIG. 28.) (according to the procedure of Hatfull et al., *Proc. Nat. Acad. Sci.*, 83:5429–5433 (1986)). One of the daughter molecules contains the L5 attP site and gene 71, and the other daughter molecule contains the int gene and the aph (kanamycin resistance) gene.

*M. smegmatis* was then transformed by electroporation (Snapper, et al. (1988)) with pMH35 which had been resolved into the circular DNA molecules as hereinabove described. Transformants selected by L5c(d1) infection occurred at an approximately 10-fold higher frequency than those selected with kanamycin according to the procedure of Snapper, et al. (1988). Also, 83% of the phage-selected transformants containing the resolved pMH35 were kanamycin sensitive, thus indicating that the circular DNA molecules carrying the int gene and aph gene, but lacking an attP site and a mycobacterial origin of replication had been lost. This was determined by the following hybridization study:

*M. smegmatis* strain mc$^2$155 was transformed with pMH9.4 (as a control), pMH35 (unresolved), or pMH35 resolved with purified resolvase in vitro.

Organisms transformed with pMH9.4 were selected with kanamycin, and organisms transformed with pMH35 (either resolved or unresolved) were selected for L5c(d1) resistance. Transformants were then selected for sensitivity or resistance to kanamycin by patch plating. All pMH9.4 and unresolved pMH35 transformants were resistant to kanamycin. 83% of the transformants which were transformed with resolved pMH35 were sensitive to kanamycin and the remainder were resistant. The kanamycin resistant transformants (17% of the population) may be a small population of organisms transformed with pMH35 which had not been resolved.

DNA from: (a) two separate *M. smegmatis* mc$^2$155 non-transformed organisms; (b) two separate *M. smegmatis* mc$^2$155 organisms transformed with pMH9.4; (c) two separate *M. smegmatis* mc$^2$155 organisms transformed with unresolved pMH35; (d) two separate *M. smegmatis* mc$^2$155 organisms transformed with resolved pMH35; and (e) two separate *M. smegmatis* mc$^2$155 organisms from the 17% of the transformed cell culture hereinabove described which included transformants that were transformed with resolved pMH35; however, these organisms were transformed with pMH35 DNA which was not resolved.

Figure 29:
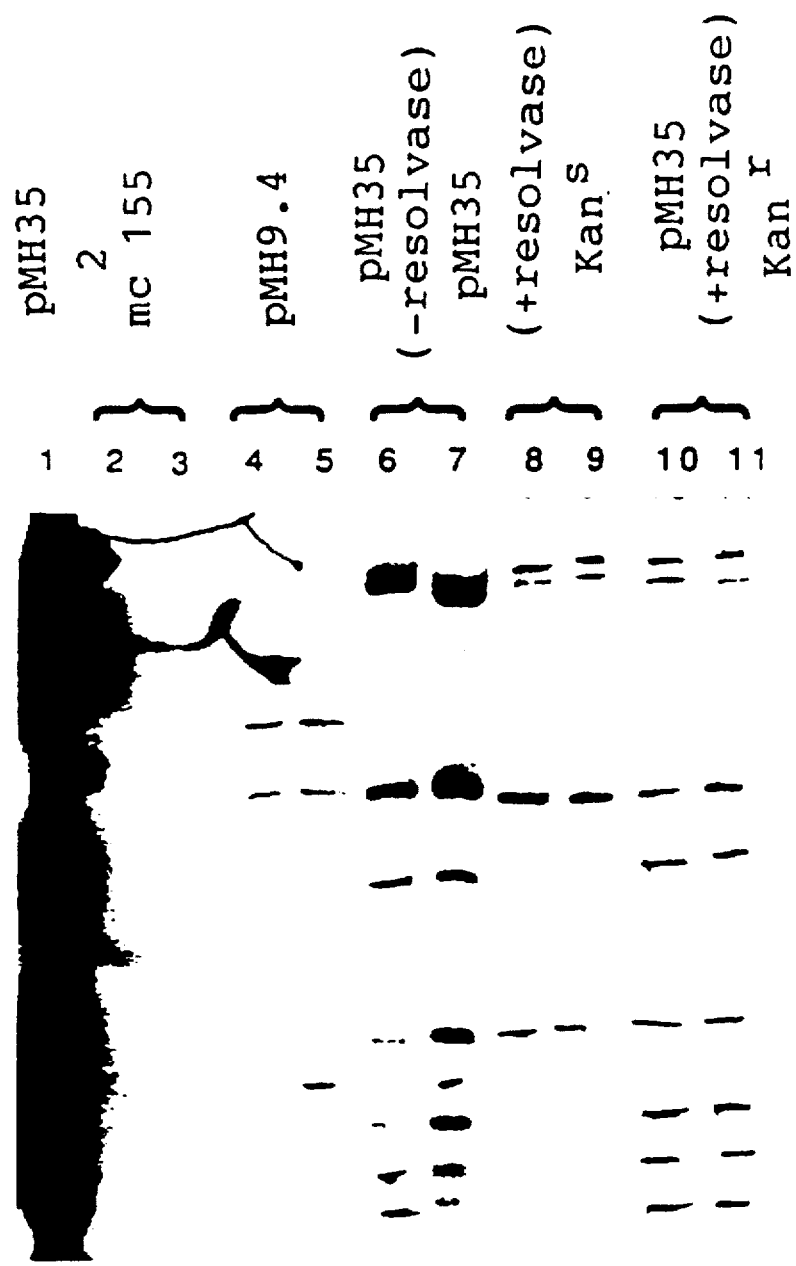
FIG. 29 is an autoradiograph showing a pattern of bands of DNA seen with kanamycin-sensitive transformants which were transformed with resolved pMH35 DNA (lanes 8 and 9) and an additional pattern of bands in transformants which were transformed with unresolved pMH35.

The DNAs were cut with BamHI and SspI, and electrophoresed on a standard 1% agarose gel. The DNAs were then transferred to nitrocellulose and hybridized with radiolabelled DNA. The autoradiograph of the nitrocellulose filter (FIG. 29) indicates that the pattern of bands seen with the kanamycin-sensitive transformants which were transformed with resolved pMH35 DNA (lanes 8 and 9) is consistent with these transformants arising from the expected products of in vitro resolution of pMH35. Additional bands are also present in the DNA from the organisms that were selected with L5c(d1), as shown in lanes 6 through 11. The sizes of these bands are consistent with their arising from a resident L5c(d1) prophage. Thus such organisms are L5 lysogens.

Lanes 6, 7, 10, and 11 include five bands which are not present in lanes 8 and 9. These bands may correspond to elements present (such as kanamycin resistance) in unresolved pMH35, but are lost after resolution of pMH35 into two singly-linked circular DNA portions.

EXAMPLE 5

Selection of pMH35 in BCG Using D29 as a Selecting Phage.

BCG organisms were electroporated with pMH35. Following a 3 hr. expression period, the organisms were plated on 7H9 media containing ADC enrichment and 10$^{10}$ D29 phages. After 3 weeks incubation, BCG colonies immune to D29 infection were found in an amount of 10$^4$ colony forming units per μg of DNA. No colonies were found for BCG transformed with a control vector pMV261. (Stover et al., *Nature*, 351:456–460 (Jun. 6, 1991)) which does not include DNA encoding phage immunity.

EXAMPLE 6

Figure 40:
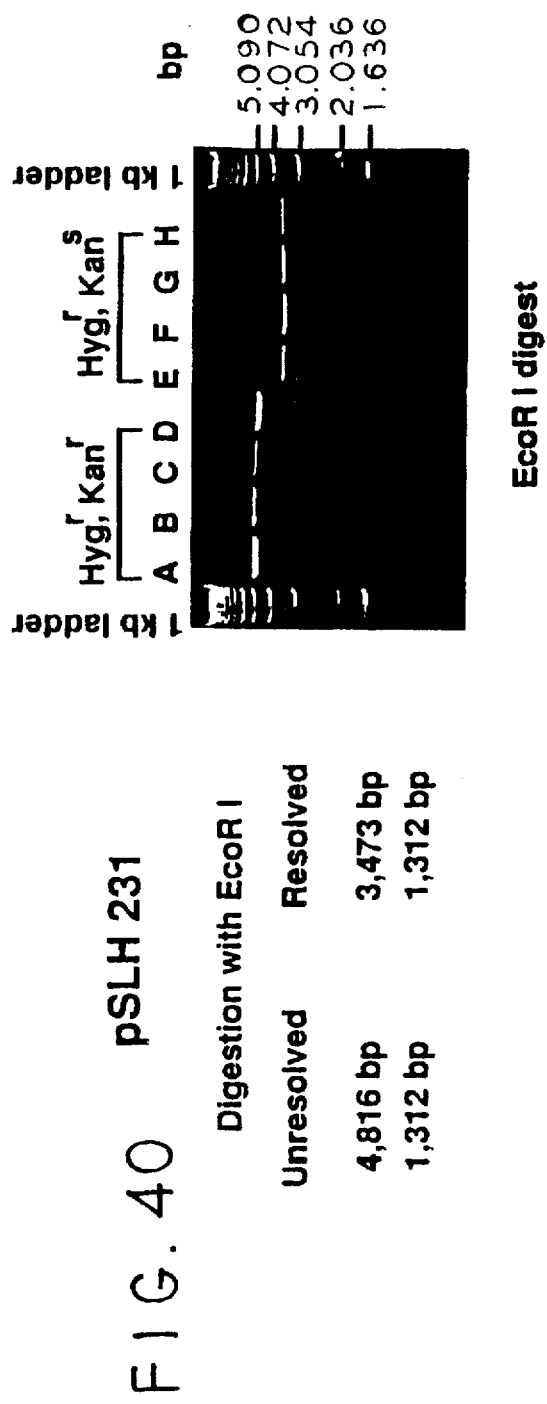
FIG. 40 shows the results of a restriction analysis of pSLH231 digested with EcoRI confirming the deletion of the $Kan^r$ gene from transformants which developed sensitivity to kanamycin as described in Example 6.
Figure 41:
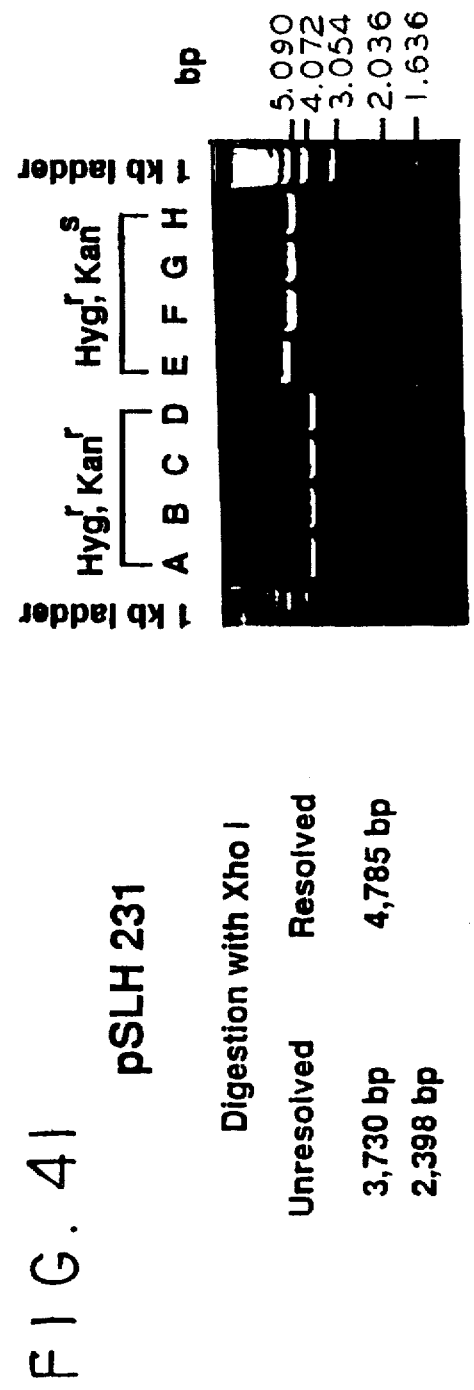
FIG. 41 shows the results of a restriction analysis of pSLH231 digested with XhoI confirming the deletion of the $Kan^r$ gene from transformants which developed sensitivity to kanamycin as described in Example 6.

In vivo Deletion of Antibiotic Resistance Markers from *Mycobacterium smegmatis* and *M. bovis* using γδ Resolvase Drug selection is not required for immunogenicity of foreign antigens delivered by rBCG, and presence of these markers presents a safety concern for rBCG use in humans. Self-catalyzed deletion of drug markers by site-specific DNA recombinases has been shown to be effective in the construction of genetically engineered crop plants (Goldsbrough et al., *Biotechnology*, 11:1286, 1993,) but no system similar to this has been applied to live vaccine vehicles. This example demonstrates a strategy to spontaneously delete the $Kan^r$ gene from rBCG in a directed fashion using γδ resolvase.

An integrating vector, pSLH223 (FIG. 31), was constructed which expresses resolvase under the control of the BCG hsp60 promoter, and contains the $Kan^r$ gene flanked by res sites, the substrates for resolvase activity. This system was tested in both fast-growing *M. smegmatis* and BCG. Initial selection after transformation was made on plates in the presence of kanamycin. Colonies were picked and passaged in medium without kanamycin and plated on medium with and without kanamycin. One third of the *M. smegmatis* and approximately 25% of the BCG transformants were found to be sensitive to kanamycin indicating the loss of $Kan^r$gene. To determine if resolvase can function in trans a plasmid that replicates extrachromosomally in mycobacteria, pSLH231, was constructed containing, in addition to the $Kan^r$ gene flanked by res sites, a second hygromycin resistance marker. The experiments reported here show that resolvase integrated into the chromosome, and functional in cis, can also be functional for the deletion of $Kan^r$ gene in trans. This versatile system for the directed deletion of drug resistance markers from rBCG eliminates the safety concern regarding such markers in this live vaccine vehicle, and is likewise applicable to other live recombinant vaccine organisms.

Integrating Vector for Autocatalytic Deletion of $Kan^r$ in cis

An integrating vector pSLH 223 was constructed and expresses resolvase under the control of the BCG hsp60 promoter and contains the $Kan^r$ promoter and contains the $Kan^r$ flanked by the res sites, the substrate of resolvase activity. The plasmid also contains the attP-int locus of mycobacteriophage L5 promoting the unidirectional integration into the attB site. After transformation, initial selection of bacteria harboring the plasmid was made on plates containing kanamycin. Kanamycin resistant colonies were picked and then passaged without antibiotic selection. Resolvase acts on the res sites to excise the $Kan^r$ gene, thereby deleting the antibiotic resistance marker. Release of kanamycin selection allows isolation of these $Kan^s$ recombinants.

Identification of Recombinant *M. smegmatis:*223

Referring to FIG. 32, twenty-four $Kan^r$ colonies, isolated after transformation and kanamycin selection, were grown and passaged in Dubos-ADC media without kanamycin. Samples (5 μl) from each passage were spotted in duplicate on Middlebrook-ADC plates with and without kanamycin. One third of the samples developed sensitivity to kanamycin after four passages consistent with the deletion of $Kan^r$ gene. Four samples were re-grown and plated for single colony isolation. Twenty-four colonies from each of the four samples were again tested for sensitivity to kanamycin. 100% of the subclones were sensitive to kanamycin (data not shown).

Detection of Resolvase Gene in Recombinant *M. smegmatis:*223

Referring to FIG. 33, PCR was performed with genomic DNA isolated from four *M. smegmatis:*223 transformants (lanes B–E), pSLH174 plasmid (identical to pSLH223 except that the $Kan^r$ gene is not flanked by res sites, lanes F), or no DNA (lane G) and resolvase-specific primers. A sample (10 μl) of each reaction was analyzed on a 1% agarose gel containing ethidium bromide. As shown in FIG. 33, a single band (600 bp) was detected in lanes B–F indicating the presence of the resolvase gene. Molecular size markers (1 kb ladder, BRL) are present in lanes A and H.

Identification of Recombinant BCG:223

Referring to FIG. 34, twenty-four $Kan^r$ colonies, isolated after transformation and kanamycin selection, were grown and passaged in Dubos-ADC media without kanamycin. Eleven stable transformants survived after four passages. Samples (5 μl) from each passage were spotted on Middlebrook-ADC plates with and without kanamycin. Four of the transformants developed sensitivity to kanamycin consistent with the deletion of the $Kan^r$ gene.

Detection of Resolvase Gene in Recombinant BCG:223

Referring to FIG. 35, PCR was performed with genomic DNA isolated from two rBCG:223 transformants (lanes B and C), non-recombinant BCG genomic DNA (Pasteur substrain, lane d), pSLH 174 plasmid (identical to pSLH 223 except that $Kan^r$ gene is not flanked by res sites, lane E), or no DNA (lane F) and resolvase-specific primers. A sample (10 μl) of each reaction was analyzed on a 1% agarose gel containing ethidium bromide. A single band (~600 bp) was detected in lanes B, C and E indicating the presence of the resolvase gene. Molecular size markers (1 kb ladder, BRL) are present in lanes A and G.

Confirmation of $Kan^r$ Gene Deletion in rBCG:223 by Southern Hybridization

Referring to FIG. 36, genomic DNA isolated from two BCG:223 transformants and BCG:162 was digested with EcoR I, Hind III, Kpn I and Pst I, separated on a 1% agarose gel, and transferred onto Nylon membrane (Boehringer Mannheim). BCG:162 harbors an integrated plasmid containing the $Kan^r$ gene that is not flanked by res sites (positive control). The $Kan^r$ gene cassette labeled with DIG (digoxigenin-11-UTP) was used as a probe for hybridization. The absence of DNA bands in the BCG:223 samples indicates the deletion of $Kan^r$ gene.

Deletion of $Kan^r$ gene in trans

To determine if resolvase expressed after chromosomal integration can act in trans to remove the $Kan^r$ gene from extrachromosomally replicating plasmids, pSLH 231 (FIG. 38) and pSLH 211r (FIG. 39) were constructed and transformed into *M. smegmatis:*223 and BCG:223. In addition to the $Kan^r$ gene flanked by res sites, the vectors contain a second marker gene. pSLH 231 contains a second hygromycin resistance marker, and pSLH 211r carries the gene for lipoprotein OspA from *Borrelia burgdorferi*. After transformation, colonies were selected by growing in the presence of kanamycin. *M. smegmatis* colonies were picked and passaged in media containing hygromycin but without kanamycin. BCG transformants were picked and passaged without antibiotic selection. Resolvase acts on the res sites to excise the $Kan^r$ gene from the plasmids, thereby deleting the antibiotic resistance marker. The absence of kenamycin selection allows isolation of $Kan^8$ recombinants.

Restriction Analysis of pSLH 231 from 231/M. smegmatis:223 Transformants Plasmid DNA isolated from four Hyg$^r$, Kan$^r$ and four Hyg$^r$, Kan$^s$ colonies of 231/M. smegmatis:223 transformants was used to transform E. coli (DH5α) for plasmid amplification. Plasmid DNA was isolated and digested with either EcoR I (FIG. 40) or Xho I (FIG. 41). Restriction analysis confirmed the deletion of the Kan$^r$ gene from the transformants which developed sensitivity to kanamycin.

Figure 42:
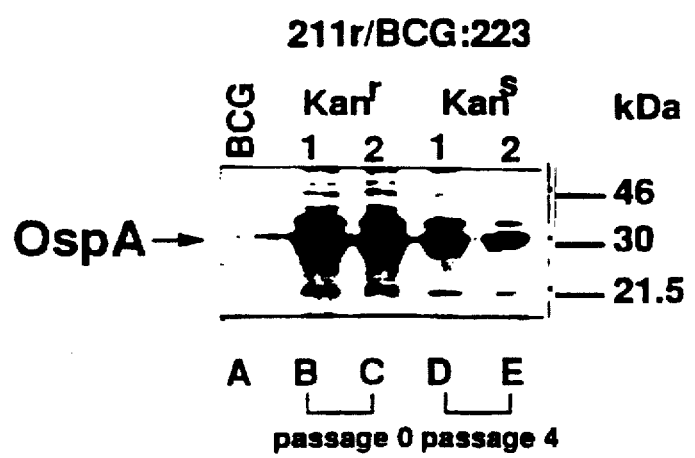
FIG. 42 shows the expression of B.burdorferi OspA antigen from 211r/BCG:223 transformants after $Kan^r$ deletion.

Expression of Borrelia burgdorferi OspA Antigen from 211r/BCG:223 Transformants after Kan$^r$ Deletion Referring to FIG. 42, eight colonies, isolated after transformation and kanamycin selection, were grown in Dubos-ADC media without kanamycin. Lysates were prepared from non-recombinant BCG (Pasteur, lane A) and the transformants for Western analysis to detect the expression of OspA. Two of the samples which expressed OspA antigen (lanes B and C) but were still resistant to kanamycin were passaged again in media without kanamycin. Lysates from the same transformants which developed sensitivity to kanamycin after passage 4 (>20 generations) were analyzed again for the expression of OspA by Western blotting (lanes D and E). Sizes of molecular weight standards (Rainbow markers, Amersham) are indicated on the right. Detection of OspA antigen in lanes D and E indicates that pSLH 211r is stable in BCG without kanamycin selection up to a minimum of 20 generations.

Discussion

In summary, we have shown that the res-resolvase system functions effectively to delete the Kan$^r$ marker gene from recombinant M. smegmatis and BCG after the initial antibiotic selection. Resolvase was effective at deleting res-flanked DNA both in cis and in trans. We are currently working to optimize expression of foreign antigens from res-resolvase integrating vectors in rBCG, including the development of stronger promoters than those used in mycobacterial vectors to date. We have recently shown, and reported here, that high-level expression from an extrachromosomal res-resolvase vector system is also feasible, and will continue to monitor the in vitro and in vivo stability of this expression vector now free of drug markers.

It is to be understood, however, that the scope of the present invention is not to be limited to the specific embodiments described above. The invention may be practiced other than as particularly described and still be within the scope of the accompanying claims.

What is claimed is:

1. A vector comprising a nucleotide sequence encoding an antibiotic resistance phenotype flanked by res sites.

2. The vector of claim 1 which further comprises a nucleotide sequence encoding an attP site and a nucleotide sequence encoding integrase.

3. The vector of claim 1 which further comprises a promoter.

4. The vector of claim 3 wherein the promoter is a mycobacterial promoter.

5. The vector of claim 4 wherein the mycobacterial promoter is a heat shock promoter.

6. The vector of claim 1 which further comprises a nucleotide sequence encoding a heterologous antigen.

7. A vector comprising nucleotide sequences encoding an attP site, and integrase and resolvase.

8. A prokaryote transformed with the vector of claim 1.

9. The prokaryote of claim 8 which is a mycobacterium.

10. The mycobacterium of claim 9 which has an attB site-containing chromosome.

11. The mycobacterium of claim 10 which is selected from the group consisting of Mycobacterium bovis-BCG, M. smegmatis, M. avium, M. phlei, M. fortuitum, M. lufu, M. paratuberculosis, M. habana, M. scrofalaceum, M. leprae, and M. intracellulare.

12. A mycobacterium with the vector of claim 7 integrated into the chromosome.

13. A mycobacterium with the vector of claim 7 integrated into the chromosome and which is further transformed with an extrachromosomal vector comprising a nucleotide sequence encoding an antibiotic resistance phenotype flanked by res sites.

14. The mycobacterium of claim 13 which is selected from the group consisting of Mycobacterium bovis-BCG, M. smegmatis, M. avium, M. phlei, M. fortuitum, M. lufu, M. paratuberculosis, M. habana, M. scrofalaceum, M. leprae, and M. intracellulare.

\* \* \* \* \*